US008217228B2

(12) United States Patent
Dodo et al.

(10) Patent No.: US 8,217,228 B2
(45) Date of Patent: Jul. 10, 2012

(54) DOWN-REGULATION AND SILENCING OF ALLERGEN GENES IN TRANSGENIC PEANUT SEEDS

(76) Inventors: Hortense W. Dodo, Huntsville, AL (US); Charles J. Arntzen, Ithaca, NY (US); Olga Martha Viquez, Huntsville, AL (US); Koffi N'da Konan, Huntsville, AL (US)

( * ) Notice: Subject to any disclaimer, the term of this patent is extended or adjusted under 35 U.S.C. 154(b) by 0 days.

(21) Appl. No.: 12/770,435

(22) Filed: Apr. 29, 2010

(65) Prior Publication Data

US 2011/0004959 A1 Jan. 6, 2011

Related U.S. Application Data

(60) Continuation of application No. 10/958,324, filed on Oct. 6, 2004, now abandoned, which is a division of application No. 09/715,036, filed on Nov. 20, 2000, now Pat. No. 6,943,010.

(60) Provisional application No. 60/167,255, filed on Nov. 19, 1999.

(51) Int. Cl.
*C12N 15/82* (2006.01)
*A01H 5/00* (2006.01)
*A01H 5/10* (2006.01)

(52) U.S. Cl. ........................................ 800/286; 800/313

(58) Field of Classification Search .................. 800/285, 800/286

See application file for complete search history.

(56) References Cited

U.S. PATENT DOCUMENTS

| | | | |
|---|---|---|---|
| 4,376,110 | A | 3/1983 | David et al. |
| 4,407,956 | A | 10/1983 | Howell |
| 4,458,066 | A | 7/1984 | Caruthers et al. |
| 5,026,545 | A | 6/1991 | Saint-Remy et al. |
| 5,558,869 | A | 9/1996 | Burks, Jr. et al. |
| 5,917,127 | A | 6/1999 | Willmitzer et al. |
| 5,951,984 | A | 9/1999 | Kaneko et al. |

FOREIGN PATENT DOCUMENTS

| | | | |
|---|---|---|---|
| EP | 0 116 718 | A1 | 8/1987 |
| EP | 0 242 246 | A1 | 10/1987 |
| EP | 1 235 920 | A2 | 9/2004 |
| WO | WO 84/02913 | A1 | 8/1984 |
| WO | WO 99/38978 | A1 | 8/1999 |
| WO | WO 01/36621 | A2 | 5/2001 |

OTHER PUBLICATIONS

Baulcombe, D. RNA silencing in plants. (2004) Nature. 431: 356-363.*

Krause, S. et al. Peanut varieties with reduced ARA h1 content indicating no reduced allergenicity.(2010) Mol. Nutr. Food Res. 54: 381-387.*

Tepnel BioSystems Ltd. Material Data Safety Sheet: Biokits Peanut Assay Kit. 2008.*

Altschul, et al. "Gapped BLAST and PSI-BLAST; A New Generation of Protein Database Search Programs", Nucleic Acids Research, 1997, vol. 25, No. 17, pp. 3389-3402, Oxford Univ. Press.

Beaucage, et al. "Deoxynucleoside Phosphoramidites—A New Class of Key Intermediates for Deoxypolynucleotide Synthesis", Tetrahedron Letters, 1981, vol. 22, No. 20, pp. 1859-1862, Pergamon Press Ltd.

Bechtold, et al. "In Planta *Agrobacterium* Mediated Gene Transfer by Infiltration of Adult Arabidopsis Thaliana Plants", Sciences De La Vie Life Sciences, Oct. 1993, vol. 316, No. 10, pp. 1194-1199, John Libbey Eurotext.

Beckman, et al. "Managing the Risk of Food Allergens", Food Testing & Analysis, Jun./Jul. 1999, vol. 5, No. 3, pp. 15-17, Rheometric Scientific.

Bhalla, et al. "Antisense-medicated Silencing of a Gene Encoding a Major Ryegrass Pollen Allergen". Proc. Natl, Acad. Sci., 1999, vol. 96, pp. 11676-11680, Plant Biology & Biotechnology Lab.

Bolton, et al. "A General Method for the Isolation of RNA Complementary to DNA", Aug. 1996, vol. 48, No. 8, pp. 1330-1397.

Branch, D. "A Good Antisense is Hard to Find", TIBS, 1998, vol. 23, pp. 45-50.

Bray, et al. "Expression of the β-subunit of β-conglycinin in Seeds of Transgenic Plants", Plants, 1987, vol. 172, pp. 364-370, Springer-Verlag.

Brusslan, et al. "An Arabidopsis Mutant with a Reduced Level of cab140 RNA is a Result of Cosupression", The Plant Cell, Jun. 1983, vol. 5, pp. 667-677, American Society of Plant Physiologists.

(Continued)

*Primary Examiner* — Russell Kallis
*Assistant Examiner* — Steven Bernacki
(74) *Attorney, Agent, or Firm* — Bradley Arant Boult Cummings LLP; Nicholas J. Landau

(57) ABSTRACT

An allergen-free transgenic peanut seed is produced by recombinant methods. Peanut plants are transformed with multiple copies of each of the allergen genes, or fragments thereof, to suppress gene expression and allergen protein production. Alternatively, peanut plants are transformed with peanut allergen antisense genes introduced into the peanut genome as antisense fragments, sense fragments, or combinations of both antisense and sense fragments. Peanut transgenes are under the control of the 35S promoter, or the promoter of the Ara h2 gene to produce antisense RNAs, sense RNAs, and double-stranded RNAs for suppressing allergen protein production in peanut plants. A full length genomic clone for allergen Ara h2 is isolated and sequenced. The ORF is 622 nucleotides long. The predicted encoded protein is 207 amino acids long and includes a putative transit peptide of 21 residues. One polyadenilation signal is identified at position 951. Six additional stop codons are observed. A promoter region was revealed containing a putative TATA box located at position −72. Homologous regions were identified between Ara h2, h6, and h7, and between Ara h3 and h4, and between Ara h1P41B and Ara h1P17. The homologous regions will be used for the screening of peanut genomic library to isolate all peanut allergen genes and for down-regulation and silencing of multiple peanut allergen genes.

30 Claims, 9 Drawing Sheets

OTHER PUBLICATIONS

Burks, MD., et al. "Identification and Characterization of a Second Major Peanut Allergen, Ara h II, with use of the Sera of Patients with Atopic Dermatitis and Positive Peanut Challenge", The Journal of Allergy and Clinical Immunology, Dec. 1992, vol. 90, No. 6, Part 1, pp. 962-969, Mosby-Year Book, Inc.

Burks, et al. "Recombinant Peanut Allergen Ara h I Expression and IgE Binding in Patients with Peanut Hypersensitivity", 1994 (unpublished), Gen Bank L38853.

Burks, et al. "Recombinant Peanut Allergen Ara h I Expression and IgE Binding in Patients with Peanut Hypersensitivity", J. Clin. Invest., 1995, vol. 96, No. 4, pp. 1715-1721, Gen Bank L34402.

Burks, et al. "Recombinant Peanut Allergen Ara h I Expression and IgE Binding in Patients with Peanut Hypersensitivity", The Journal of Clinical Investigation, Oct. 1995, vol. 96, pp. 1715-1721, American Society for Clinical Investigation, Inc.

Chen, et al. "Expression and Inheritance of Multiple Transgenes in Rice Plants", Nature Biotechnology, Nov. 1998, vol. 16, No. 211, pp. 1060-1064.

Cole, S.P.C., et al. "The EBV-Hybridoma Technique and its Application to Human Lung Cancer", Monoclonal Antibodies and Cancer Therapy, 1985, pp. 77-96, Alan R. Liss, Inc.

Cote, et al. "Generation of Human Monoclonal Antibodies Reactive with Cellular Antigens", Proc. Natl. Acad. Sci., Apr. 1983, vol. 80, pp. 2026-2030, Memorial Sloan-Kettering Cancer Center.

Database GENEMGL 'Online; Sep. 27, 1996 I Jaabg B,J, -: "Expression vector pNEX3 beta-lactamase mRa, complete cds." XP002167602; Accession EVU67091.

Datla, et al. "A Bifunctional Fusion Between β-Glucuronidase and Neomycin Phosphotransferase: A Broad-Spectrum Marker Enzyme for Plants", Gene, 1991 vol. 101, No. 2, pp. 239-246, Elsevier Sci. Pub.

De Framond, et al. "Mini-Ti: A New Vector Strategy for Plant Genetic Engineering", Biotechnology, May 1983, pp. 262-269, National Library of Medicine.

De Jong, et al. "Identification and Partial Characterization of Multiple Major Allergens in Peanut Proteins", Clinical and Experimental Allergy, 1998, vol. 28, pp. 743-751, Blackwell Science Ltd.

De La Pena, et al. "Transgenic Rye Plants Obtained by Injecting DNA into Young Floral Tillers", Nature, 1987, vol. 325, No. 6101, pp. 274-276, Kenya Rift Structure.

De St. Groth, et al. "Production of Monoclonal Antibodies: Strategy and Tactics", Journal of Immunological Methods, 1980, vol. 35, pp. 1-21, Elsevier/North-Holland Biomedical Press.

Deblaere, et al. "Vectors for Cloning in Plant Cells", Methods in Enzymology, 1987, vol. 153, pp. 277-293, Academic Press, Inc.

Dodo, et al. "cDNA Clone of a Putative Peanut (Arachis hypogaea L.) Trypsin Inhibitor has Homology with peanut Allergens Ara h 3 and Ara h 4", Journal of Agricultural and Food Chemistry, Mar. 10, 2004, vol. 52, No. 5, pp. 1404-1409, American Chemical Society.

Elliston, et al. "The Molecular Architecture of Plant Genes and Their Regulation", Plant Biotechnology, 1989, pp. 115-139, Butterworth Publishers.

Engvall, E. "Enzyme Immunoassay ELISA and EMIT", Immunochemical Techniques, 1980, vol. 70, pp. 419-439, Academic Press, Inc.

Fire, et al. "Potent and Specific Genetic Interference by Double-Stranded RNA in *Caenorhabditis elegans*", Nature, Feb. 1998, vol. 391, pp. 806-811.

Fromm, et al. "Expression of Genes Transferred into Monocot and Dicot Plant Cells by Electroporation", Proc. Natl. Acad. Sci., Sep. 1985, vol. 82, pp. 5824-5828, Dept. of Biological Sciences.

Kohler, G., et al. "Continuous Cultures of Fused Cells Secreting Antibody of Predefined Specificity", Nature, Aug. 1975, vol. 256, pp. 495-497, National Institute of Health.

Goeddel, et al. "Synthesis of Human Fibroblast Interferon by *E. coli*", Nucleic Acids Research, 1980, vol. 8, No. 18, pp. 4057-4075, IRL Press Limited.

Greger, et al. "Poly(A) Signals Control Both Transcriptional Termination and Initiation Between the Tandem GAL10 and GAL7 Genes of *Saccharomyces cerevissiae*", the EMBO Journal, 1998, vol. 17, No. 16, pp. 4771-4779, Oxford University Press.

Hoekema, et al. "A Binary Plant Vector Strategy Based on Separation of vir and T-region of the *Agrobacterium tumefaciens* Ti-plasmid", Nature, May 1983, vol. 303, No. 5913, pp. 179-180, Macmillan Journals Ltd.

Horsch, et al. AAAS Annual Meeting Preliminary Program, Mar. 1985, pp. 1229-1231, American Peanut Research and Education Society, Inc., 1991 Proceedings, vol. 23, p. 30.

Jefferson, et al. "GUS fusions β-glucuronidase as a Sensitive and Versatile Gene Fusion Marker in Higher Plants", The EMBO Journal, 1987, vol. 6, No. 13, pp. 3901-3907, IRL Press Ltd.

Kaang. "Parameters Influencing Ectopic Gene Expression on Aplysia Neurons", Inst. For Mol. Biol. & Genet, (published) 1996, Gen Bank U67091.

Keating, MD, et al. "Immunoassay of Peanut Allergens in Food Processing Materials and Finished Foods", The Journal of Allergy and Clinical Immunology, Jul. 1990, vol. 86, No. 1, pp. 41-44, Mosby-Year Book, Inc.

Kennerdell, et al. "Use of dsRNA-Medicated Genetic Interference to Demonstrate that Frizzled and Frizzled 2 Act in the Wingless Pathway", Cell, Dec. 1998. vol. 95, pp. 1017-1026, Cell Press.

Kleber-Janke. "Selective Cloning of Peanut Allergens, including Profilin and 2S Albumins, by Phage Display Technology", Int. Arch. Allergy Immunol. 119, 1998, pp. 265-274, Gen Bank AF086821.

Kleber-Janke. "Selective Cloning of Peanut Allergens, including Profilin and 2S Albumins, by Phage Display Technology", Int. Arch. Allergy Immunol. 119, 1988, pp. 265-274, Gen Bank AF092846.

Kleber-Janke, et al. "Selective Cloning of Peanut Allergens, including Profilin and 2S Albumins, by Phage Display Technology", International Archives of Allergy and Immunology, Aug. 1999, vol. 119, pp. 265-274, S. Karger AG. Basel.

Kleber-Janke. "Selective Cloning of Peanut Allergens, including Profilin and 2S Albumins, by Phage Display Technology", Int. Arch. Allergy Immunol., 1999, 119, pp. 265-274, Gen Bank AF089616.

Kleber-Janke. "Selective Cloning of Peanut Allergens, including Profilin and 2S Albumins, by Phage Display Technology", Int. Arch. Allergy Immunol. 119, pp. 265-274, 1998 Gen Bank AF091737.

Klein, et al. "High-velocity microprojectiles for delivering nucleic acids into living cells", Nature, May 1987, vol. 327, pp. 70-73, Dept. Horticultural Sciences.

Konan, et al. "Towards the Development of a Hypoallergenic Peanut through Genetic Transformation", Applied Biotechnology, Food Science and Policy, 2003, vol. 1 No. 3, pp. 1-10, Open Mind Journals Ltd.

Kozbor, et al. "The Production of Monoclonal Antibodies from Human Lymphocytes", Immunology Today, 1983, vol. 4, No. 3, pp. 72-78, Elsevier Biomedical Press.

Krapovickas, A. Domestication and Exploitation of Plant and Animals. London: Gerald Duckworth, 1969: 247.

Krebbers, et al. "Determination of the Processing Sites of an Arabidopsis 2S Albumin and Characterization of the Complete Gene Family", Plant Physiology, Aug. 1998, vol. 87, No. 4, pp. 859-865.

Lacorte, et al. "Gene Transfer into Peanut (Arachis hypogeal L.) by *Agrobacterium tumefaciens*", Plant Cell Reports, 1991, vol. 10, No. 6/7, pp. 354-357, Springer-Verlag.

Lutz et al. "The Distribution of Two hnRNP-Associated Proteins Defined by a Monoclonal Antibody Is Altered In Heat-Shocked HeLa Cells", Experimental Cell Research, 1988, vol. 175, pp. 109-124, Academic Press, Inc.

Matzke et al. "How and Why Do Plants Inactivate Homologous (Trans)genes?", Plant Physiology, Mar. 1995, vol. 107, No. 3, pp. 679-685, Laboratory of Biochemistry, National Cancer Institute.

Metcalfe, et al. "Assessment of the Allergenic Potential of Foods Derived from Genetically Engineered Crop Plants", Critical Reviews in Food Science and Nutrition, 1996, 36:165-186.

Montgomery et al. "RNA as a Target of Double-Stranded RNA-mediated Genetic Interference in *Caenorhabditis elegans*", Proc. Natl. Acad. Sci., Dec. 1998, vol. 95, pp. 15502-15507, National Academy of Sciences.

Moore, et al. "The inheritance of High Oleic Acid in Peanut", The Journal of Heredity, May/Jun. 1989, vol. 80, No. 3, pp. 252-253, National Institute of Health.

Mosbach, et al. "Formation of proinsulin by Immobilized *Bacillus subtilis*", Nature, Apr. 1983, vol. 302, No. 5908, pp. 543-545, Macmillan Journals Ltd.
Needham-Vandevanter, et al. "Characterization of an Adduct Between CC-1065 and a Defined Oligodeoxynucleotide Duplex", Nucleic Acids Research, 1984, vol. 12, No. 15, pp. 6159-6169. IRL Press Limited.
Neuhuber, et al. "Susceptibility of Transgene Loci to Homology-dependent Gene Silencing", Molecular & General Genetics, Aug. 1994, vol. 244, No. 3, pp. 230-241, Springer-Verlag.
Ngo, et al. "Double-stranded RNA Induces mRNA Degradation in *Trypanosoma brucei*", Proc. Natl. Acad. Sci., Dec. 1998, vol. 95, pp. 14687-14692, National Academy of Sciences.
Nielsen, et al. "Identification of Prokaryotic and Eukaryotic Signal Peptides and Prediction of their Cleavage Sites", Protein Engineering, 1997, vol. 10, No. 1, pp. 1-6, Oxford University Press.
Norden, et al. "Application Genetics in Peanut Variety Improvement", Florida Agricultural Research 1984, 3, pp. 16-18, Biotechnology.
Ozias-Akins, et al. "Regeneration of Transgenic Peanut Plants from Stably Transformed Embryogenic Callus", 1993, pp. 185-194, Elsevier Scientific Publishers Ireland Ltd.
Palva, et al. "Secretion of Interferon by *Bacillus subtilis*", Gene, May/Jun. 1983, vol. 22, Nos. 2 and 3, pp. 229-235, Elsevier Science Publishers.
Pawlowski et al. "Transgene Inheritance in Plants Genetically Engineered by Microprojectile Bombardment", Molecular Biotechnology, Aug. 1996, vol. 6, No. 1, pp. 17-30, Humana Press Inc.
Peleman et al. "Strong Cellular Preference in the Expression of a Housekeeping Gene of Arabidopsis Thaliana Encoding S-Adenosylmethionine Synthetase", The Plant Cell, 1989, vol. 1, pp. 81-93, American Society of Plant Physiologists.
Queen, et al. "Cell-Type Specific Regulation of a κ Immunoglobulin Gene by Promoter and Enhancer Elements", Immunological Reviews, 1986, No. 89, Munksgaard, Copenhagen, Denmark.
Rabjohn, et al. "Molecular Cloning and Epitope Analysis of the Peanut Allergen, Ara h 3" Pediatrics, University of Arkansas for Medical Sciences, (unpublished) 1998, Gen Bank AF093541.
Rabjohn, et al. "Molecular Cloning and Epitope Analysis of the Peanut Allergen Ara h 3", J. of Clinical Investigation, 1999, vol. 1, No. 4, pp. 535-542, American Society for Clinical Investigation.
Rocha-Sosa, et al. "Both Developmental and Metabolic Signals activate the Promoter of a Class I Patatin Gene", The EMBO Journal, 1989, vol. 8, No. 1, pp. 23-29, IRL Press.
Rosahl, et al. "Expression of a Tuber-specific storage Protein in Transgenic Tobacco Plants: Demonstration of an Esterase Activity", 1987, vol. 6, No. 5, pp. 1155-1159, IRL Press Ltd.
Schneider, I. "Cell Lines Derived from Late Embryonic Stages of *Drosophila melanogaster*", Journal of Embryology and Experimental Morphology, 1972, vol. 27, No. 2, pp. 353-365, Cambridge Univ. Press.
Schuch, W. "Using Antisense RNA to Study Gene Function", Molecular Biology of Plant Development, 1991, No. XLV, pp. 117-127, Society for Experimental Biology.
Shewry, et al. "Genetic Modification and Plant Food Allergens: Risks and Benefits", Journal of Chromatography, 2001 vol. 756:327-335.
Shimatake, et al. "Purified λ Regulatory Protein cII Positively Activates Promoters for Lysogenic development", Nature, Jul. 1981, vol. 292, No. 5819, pp. 128-132, Macmillan Journals Ltd.
Smith, et al. "Antisense RNA Inhibition of Polygalacturonase Gene Expression in Transgenic Tomatoes", Nature, 1988, vol. 334, No. 6184, pp. 724-726.
Southern, E.M. "Detection of Specific Sequences Among DNA Fragments Separated by Gel Electrophoresis", Journal of Molecular Biology, Nov. 1975, vol. 98, No. 3, pp. 503-517, Academic Press, Inc.
Sprague, et al. "Expression of a Recombinant DNA Gene Coding for the Vesicular Stomatitis Virus Nucleocapsid Protein", Journal of Virology, Feb. 1983, pp. 773-781, American Society for Microbiology.
Stanley. "The Major Peanut Allergen Ara h II is a Seed Storage Protein with Multiple IgE-binding Epitopes", (unpublished) 1996, Gen Bank L77197.
Stanley, et al. "Identification and Mutational Analysis of the Immunodominant IgE Binding Epitopes of the Jaor Peanut Allergen Ara h 2", Archives of Biochemistry and Biophysics, Jun. 1997, vol. 342, No. 2, pp. 244-253, Academic Press.
Tada, et al. "Reduction of 14-16 kDa Allergenic Protein in Transgenic Rice Plants by Antisense Gene", FEBS Letters, Aug. 1996, vol. 391, No. 3, pp. 341-345, Federation of European Biochemical Soc.
Tatusova, et al. "BLAST 2 Sequences, A New Tool for Comparing Protein and Nucleotide Sequences" FEMS Microbiology Letters, 1999, vol. 174, No. 2, pp. 247-250, Elsevier Science B.V.
Trentham, et al. "Effects of Oral Administration of Type II Collagen on Rheumatoid Arthritis", Science, Sep. 1993, vol. 261, pp. 1727-1730, Division of Cytokine Biology.
Vaitukaitis, et al. "A Method for Producing Specific Antisera with Small Doses of Immunogen", The Journal of Clinical Endocrinology and Metabolism, Dec. 1971, vol. 33, No. 6, pp. 988-991, Endocrine Soc.
Vasil, I. "Molecular Improvement of Cereals", Plant Molecular Biology, Sep. 1994, vol. 25, No. 6, pp. 925-937, Kluwer Academic Publishers.
Viquez, et al. "Isolation and Molecular Characterization of the First Genomic Clone of a Major Peanut Allergen, Ara H 2", Journal of Allergy Clinical Immunology, Apr. 2001, vol. 107, No. 4, pp. 713-717. Mosby, Inc.
Viquez, et al. "Structure and Organization of the Genomic Clone of a Major Peanut Allergen Gene, Ara h1" *Molecular Immunology*, 2003, vol. 40, pp. 5656-6571, Elsevier, Ltd.
Viquez, et al. "Genomic Organization of Peanut Allergen Gene, Ara h 3", Molecular Immunology, Nov. 2004, vol. 41, No. 12, pp. 1235-1240.
Waterhouse, et al. "Virus Resistance and Gene Silencing in Plants can be Induced by Simultaneous Expression of Sense and Antisense RNA", Proc. Natl. Acad. Sci., Nov. 1998, vol. 95, No. 23, pp. 13959-13964, National Academy of Sciences.
Weiner, et al. "Double-Blind Pilot Trial of Oral Tolerization with Myelin Antigens in Multiple Sclerosis", Science, Feb. 1993, vol. 259, pp. 1225-1368, American Assoc. for the Advancement of Science.

* cited by examiner

```
                                  tccttacgcgaaatacggg
 -91 cagacatggcctgcccggt**tattatta**ttttgacacagaccaac
 -46 tggtaatggtagcgaccggcgctcagctggaattcgcggccgcca
   1 atggccaagctcaccatactagtagccctcgcccttttcctcctc
      M  A  K  L  T  I  L  V  A  L  A  L  F  L  L
  46 gctgcccacgcatctgcgaggcagcagtgggaactccaaggagac
      A  A  H  A  S  A  R  Q  Q  W  E  L  Q  G  D
  91 agaagatgccagagccagctcgagagggcgaacctgaggccctgc
      R  R  C  Q  S  Q  L  E  R  A  N  L  R  P  C
 136 gagcaacatctcatgcagaagatccaacgtgacgaggattcatat
      E  Q  H  L  M  Q  K  I  Q  R  D  E  D  S  Y
 181 gaacgggacccgtacagccctagtcaggatccgtacagccctagt
      E  R  D  P  Y  S  P  S  Q  D  P  Y  S  P  S
 226 ccatatgatcggagaggcgctggatcctctcagcaccaagagagg
      P  Y  D  R  R  G  A  G  S  S  Q  H  Q  E  R
 271 tgttgcaatgagctgaacgagtttgagaacaaccaaaggtgcatg
      C  C  N  E  L  N  E  F  E  N  N  Q  R  C  M
 316 tgcgaggcattgcaacagatcatggagaaccagagcgataggttg
      C  E  A  L  Q  Q  I  M  E  N  Q  S  D  R  L
 361 caggggaggcaacaggagcaacagttcaagagggagctcaggaac
      Q  G  R  Q  Q  E  Q  Q  F  K  R  E  L  R  N
 406 ttgcctcaacagtgcggccttagggcaccacagcgttgcgacttg
      L  P  Q  Q  C  G  L  R  A  P  Q  R  C  D  L
 451 gacgtcgaaagtggcggcaggcggccgcgaattccgccgatactg
      D  V  E  S  G  G  R  R  P  R  I  P  P  I  L
 496 acgggctccaggagtcgtcgccaccaatccccatatggaaaccgt
      T  G  S  R  S  R  R  H  Q  S  P  Y  G  N  R
 541 cgatattcagccatgtgccttcttccgcgtgcagcagatggcgat
      R  Y  S  A  M  C  L  L  P  R  A  A  D  G  D
 586 ggctggtttccatcagttgctgttgactgtagcggctgatgttga
      G  W  F  P  S  V  A  V  D  C  S  G Stop
 631 actggaagtcgccgcgccactggtgtgggccataattcaattcgc
 676 gcgtcccgcagcgcagaccgttttcgctcgggaagacgtacgggg
 721 tatacatgtctgacaatggcagatcccagcggtcaaaacaggcgg
 766 cagtaaggcggtcgggatagttttcttgcggccctaatccgagcc
 811 agtttacccgctctgctacctgcgccagctggcagttcaagccaa
 856 tccgcgccggatgcggtgtatcgctcgccacttcaacatcaacgg
 901 taatcgccatttgaccactaccatcaatccggtaggttttccggc
 946 tgataaataaaggttttcccctgatgctgccacgcgtgagcggtc
 991 gtaatcagcaccgcatcaacaagtgtattttgccgtgcactgcaa
1036 caacgctggttcgggctg
```

gacacagaccaactggtaatggtagcgaccggcgctcagctggaattcgcggccgccaatggccaagc
tcaccatactagtagccctcgcccttttcctcctcgctgcccacgcatctgcgaggcagcagtgggaactccaaggagacagaa
gatgccagagccagctcgagagggcgaacctgaggccctgcgagcaacatctcatgcagaagatccaacgtgacgaggattc
atatgaacgggacccgtacagccctagtcaggatccgtacagccctagtccatatgatcggagaggcgctggatcctctcagca
ccAAGAGAGGTGTTGCAATGAGCTGAACGAGTTTGAGAACAACCAAAGGTGC
ATGTGCGAGGCATTGCAACAGATCATGGAGAACCAGAGCGATAGGTTGCAG
GGGAGGCAACAGGAGCAACAGTTCAAGAGGGAGCTCAGGAACTTGCCTCAA
CAGTGCGGCCTTAGGGCACCACAGCGTTGCGACTTGGACGTCGAAAGTGGC
GGCAGgcggccgcgaattccgccgatactgacgggctccaggagtcgtcgccaccaatccccatatggaaaccgtcgat
attcagccatgtgccttcttccgcgtgcagcagatggcgatggctggtttccatcagttgctgttgactgtagcggctga

Fig. 4.

atggctaagcttcttgagctttctttttgcttttgctttctagttctgggagctagcagcatctccttcaggcagcagcc
ggaggagaatgcgtgccagttccagcgcctcaatgcgcagagacctgacaaccgcattgaatcggagggcggttacattg
agacttggaaccccaacaaccaggagttcgaatgcgccggcgtcgccctctctcgcttagtcctccgccgcaacgccctt
cgtaggcctttctactccaatgctccccaggagatcttcatccagcaaggaaggggatactttgggttgatattccctgg
ttgtcctagcacatatgaagagcctgcacaacaaggacgccgatatcagtcccaaagaccaccaagacgtttgcaagaag
aagaccaaagccaacagcaacaagatagtCACCAGAAGGtGCACCGTTTCaATGAGGGTGATC
TCATTGCAGTTCCCACCGGTGTTGCTTTctggctgtACAACGACCACGACACTGAT
GTTGTTGCTGTTTCTCTTACTGACACCAACAACAACGACAACCAGCTTGATCA
GTTCCCCAGGAGATTCAATTTGGCTGGGAACcacgAGCAAGAGTTCTTAAGGTA
CCAGCAACAAAGCAGACAAAGCAGACGAAGAAGCTTACCATATAGCCCATA
CAGCCCGCAtaGTCgGCCTAGACgAGAAGAGCGTGAATTTcGCCCTCGAGGACA
GCACAGCCGCAGAGAACGAGCAGGACAAGAAGAAGAAgACGAAGGTGGAA
ACATCTTCAGCGGCTTCACGCCGGAGTTCCTGGAACAAGCCTTCCAGGTTGA
CGACAGACAGATtGTGCAAAAtCTGTGGGGCGAGAaCGAGAGTGAAGAAGAG
GGAGCCATTGTGACggTGAGGGGAGGCCTCAGAATCTTGAGCCCAGATggaacga
gaggTGCCGACGAAGAAGAGGAATACGATGAAGATcAATATGAATACcATGAA
cAGGATgGAAGGCGTGGCAGGGGAAGCAGAGGCGGGGGAATGGTATTGAA
GAGACGATCTGCACCGCAtgtGTTAAAAAGAACATTGGTgGAAACAGATCCCCT
cACATCTACgatcCTCAGCGCTGGTTCACTCAAAACTGCCACGATCTCAACCTTC
TAATCCTTAGGTGGCTTGGACTTAGTGctgaatatggaaatctctacaggaatgcattgtttgtccctcac
tacaacaccaacgcacacagcatcatatatgcattgaggggacgggctcacgtgcaagtggtggacagcaacggcaacagag
tgtacgacgaggagcttcaagagggtcacgttcttgtggtgccacagaacttcgccgtggctgggaagtcccagagcgagaac
ttcgaatacgtggcattcaagacagattcaaggcccagcatagccaactttgccggtgaaaactccttcatagataacctgccgg
aggaggtggttgcaaattcatatggcctcccaagggagcaggcaaggcagcttaagaacaacaaccccttcaagttcttcgttcc
accttttcagcagtctccgagggctgtggcttaaaaacgaccagtatcttttgcaagcgtgttatccactaacataactttttgccaca
aatgaataatataataataagaagaataatgtagttttaatttttagtatgaataagaatacaaaggggcattgatgcctttttgtttaag
atcggaatgtaacatatgtgcaatgagcagatatggagaaaacctttttgcgggaaaaacatgaataataaaagaagttatggtctc
acgcaaaaaaaaaaaaaaaaaaaaa

Fig. 5.

aataatcatatatattcatcaatcatctatataagtagtagcaggagcaatgagagggagggtttctccactgatgctgt
tgctagggatccttgtcctggcttcagtttctgcaacgcatgccaagtcatcaccttaccagaagaaaacagagaacccc
tgcgcccagaggtgcctccagagttgtcaacaggaaccggatgacttgaagcaaaaggcatgcgagtctcgctgcaccaa
gctcgagtatgatcctcgttgtgtctatgatcctcgaggacacactggcaccaccaaccaacgttcccctccaggggagc
ggacacgtggccgccaacccggagactacgatgatgaccgccgtcaaccccgaagagaggaaggaggccgatggggacc
agctggaccgagggagcgtgaaagagaagaagactggagacaaccaagagaagattggaggcgaccaagtcatcagcagc
cacggaaaataaggcccgaaggaagagaaggagaacaagagtggggaacaccaggtagccatgtgagggaagaaacatct
cggaacaaccctttctacttcccgtcaaggcggtttagcacccgctacgggaaccaaaacggtaggatccgggtcctgcag
aggtttgaccaaaggtcaaggcagtttcagaatctCCAGAATCACCGTATTGTGCAGATCGAGGCC
AaaCCTAACACTCTTGTTCTTCCCAAGCACGCTGATGCTGATAACATCCTTGTT
ATCCAGCAAGGgcAAGCCACCGTGACCGTAGCAAATGGCAATAACAGAAAGA
GCTTTAATCTTGACGAGGGCCATGCACTCAGAATCCCATCCGGTTTCATTTCC
TACATCTTGAAccgcCATGACAACCAGAACCTCAGAGTAGCTAAAATCTCCATG
CCCGTTAACACacccggccagtttgaggatttcttcccggcgagcagccgagaccaatcatcctacttgcagggcttc
agcaggaatacgttggaggccgccttcaatgcggaattcaatgagatacggagggtgctgttagaagagaatgcaggaggtga
gcaagaggagagagggcagaggcgatggagtactcggagtagtgagaacaatgaaggagtgatagtcaaagtgtcaaagga
gcacgttgaagaacttactaagcacgctaaatccgtctcaaagaaaggctccgaagaagagggagatatcaccaacccaatca
acttgagagaaggcgagcccgatctttctaacaactttgggaagttatttgaggtgaagccagacaagaagaacccccagcttca
ggacctggacatgatgctcacctgtgtagagatcaaagaaggagctttgatgctcccacacttcaactcaaaggccatggttatc
gtcgtcgtcaacaaaggaactggaaaccttgaactcgtggctgtaagaaaagagcaacaacagaggggacggcgggaagaa
gaggaggacgaagacgaagaagaggagggaagtaacagagaggtgcgtaggtacacagcgaggttgaaggaaggcgatg
tgttcatcatgccagcagctcatccagtagccatcaacgcttcctccgaactccatctgcttggcttcggtatcaacgctgaaaaca
accacagaatcttccttgcaggtgataaggacaatgtgatagaccagatagagaagcaagcgaaggatttagcattccctgggtc
gggtgaacaagttgagaagctcatcaaaaaccagaaggaatctcactttgtgagtgctcgtcctcaatctcaatctcaatctccgtc
gtctcctgagaaagagtctcctgagaaagaggatcaagaggaggaaaaccaaggagggaagggtccactcctttcaatttgaa
ggcttttaactgagaatggaggcaacttgttatgtatcgataataagatcacgcttttgtactctactatccaaaaacttatcaataaat
aaaaacgtttgtgcgttgtttctcc Figure 6: Gene constructs for down-regulating peanut allergens in transgenic peanuts.

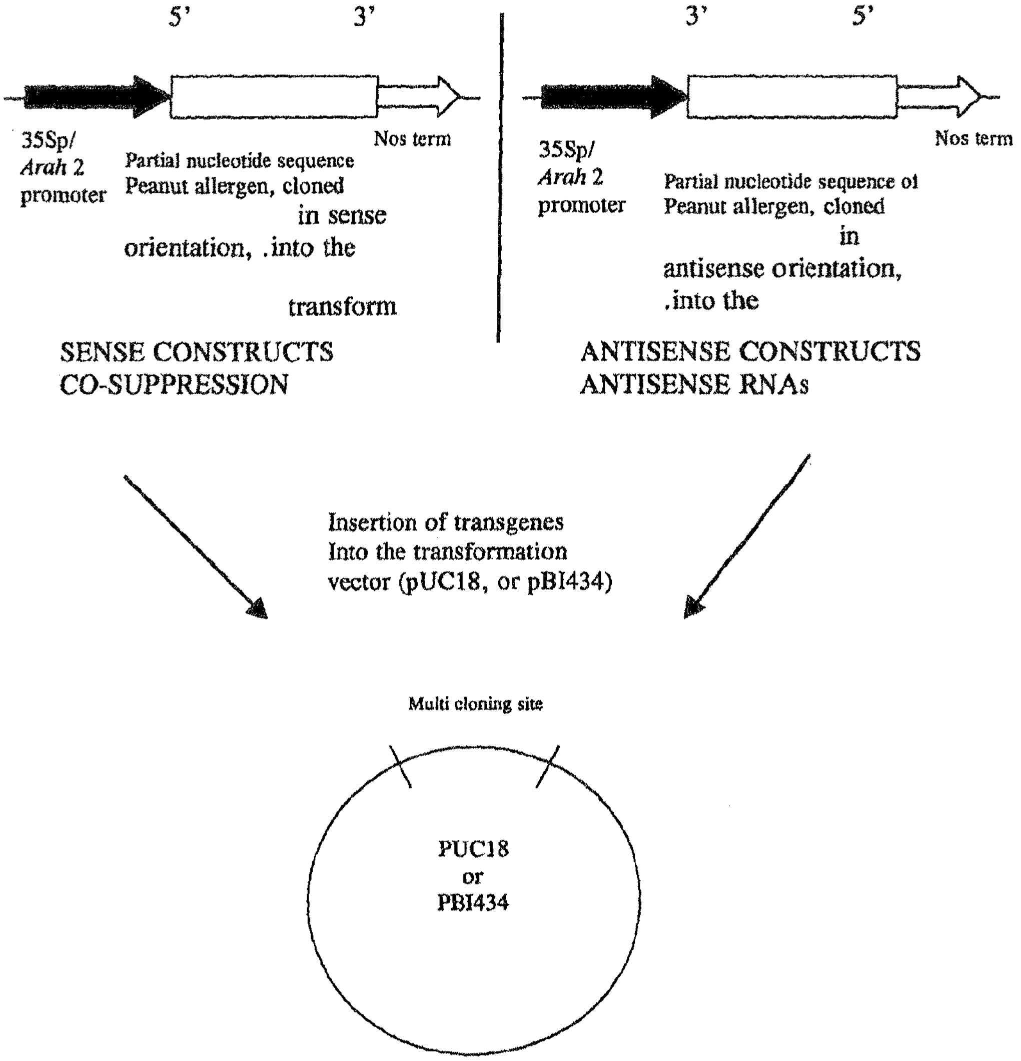

| 5'  3' | 3'  5' |
|---|---|
| 35Sp/ Arah 2 promoter — Partial nucleotide sequence Peanut allergen, cloned in sense orientation, .into the transform — Nos term | 35Sp/ Arah 2 promoter — Partial nucleotide sequence of Peanut allergen, cloned in antisense orientation, .into the — Nos term |
| SENSE CONSTRUCTS CO-SUPPRESSION | ANTISENSE CONSTRUCTS ANTISENSE RNAs |

Insertion of transgenes
Into the transformation
vector (pUC18, or pBI434)

Multi cloning site

PUC18
or
PBI434

Figure 7.

agaaagagaagacaagatgtcgtggcaaacctacgtcgataaccaccttctctgcgaaattgaaggcgaccacctctcct
ccgccgcaatcctcggccaagacggcggtgtttgggctcagagctctcatttccctcagttcaagcctgaggaaattact
gctatcatgaacgactttgctgagcctggatcgctcgcccctaccgggttgtacctcggtggcaccaaatacatggttat
ccaaggtgaacccggagctatcattccagggaagaagggtcctggtggtgttaccattgagaagacgaatcaggcgtta
atcatcggaatctacgataagccaatgactccggggcagtgcaacatgattgttgaaaggctgggtgattatctcattga
tacgggtctttaagtcctctttgttatttcttgttatctgcttgcttatttcactggctcctatacgaggcttcgcatcgatgtgccaaga
gaatgctcgattgtagtgtaataatattaattgatgggtattcaaaagtcatgggatctgcgtctagggaagaagttatggtgcttga
gaagtgaatgataactatcatctctgttgttgtgcttttagcgggtatctgtatacaatttacaagtggttttaatgctgtgggcataaa
tgggcattaaaaaaaaaaaaaaaaaaaaaaaaaaaaaaaaaaaaaaaaaaaaaaaaaaaaaaaaaaaaaaaaaaaaaaaaaa

Fig. 9

```
                               tccttacgcgaaatacggg
-91 cagacatggcctgcccggttattattatttttgacacagaccaac
-46 tggtaatggtagcgaccggcgctcagctggaattcgcggccgcca
  1 atggccaagctcaccatactagtagccctcgcccttttcctcctc
```

Fig. 9 shows the nucleotide sequence of the *Arah2* promoter upstream of the ATG initiation codon of the genomic *Arah2* clone.

DOWN-REGULATION AND SILENCING OF ALLERGEN GENES IN TRANSGENIC PEANUT SEEDS

CROSS-REFERENCE TO RELATED APPLICATIONS

This application is a continuation of U.S. application Ser. No. 10/958,324, filed on Oct. 6, 2004 now abandoned. U.S. application Ser. No. 10/958,324 is a divisional application under 35 U.S.C. §121 of U.S. application Ser. No. 09/715,036, filed on Nov. 20, 2000, which is now issued as U.S. Pat. No. 6,943,010. U.S. application Ser. No. 09/715,036 cites the benefit of U.S. Provisional Patent Application 60/167,255, filed Nov. 19, 1999, which is now expired. All of the foregoing U.S. Patents and U.S. Patent Applications are incorporated herein by reference in their entireties.

STATEMENT OF GOVERNMENT FUNDING

This invention was made with Government support under Grant No. 96-02658 awarded by the United States Department of Agriculture Cooperative States Research Education and Extension Services (USDA/CSREES) Capacity Building Program. The Government has certain rights in the invention.

FIELD OF THE INVENTION

This invention relates to transgenic peanut cells, peanut seeds and peanut products with reduced or undetectable quantities of one or more peanut allergen proteins. The invention also relates to isolated DNA sequences coding for peanut allergen proteins, as well as antisense, genes corresponding to each of the allergen protein genes. Furthermore, the invention relates to recombinant methods of reducing, and eliminating one or more of the peanut allergens in peanut seeds.

BACKGROUND OF THE INVENTION

Food allergy is a serious health problem, and can be life threatening. Public awareness of food allergies is at an all-time high, in part due to the fact that allergic reactions to foods are being reported more frequently. Up to 160 foods have been found to cause allergic reactions (Hefle, 1996, *Crit. Rev. Food Sci. Nutr.* 36:69-89).

The most common allergen-containing foods are peanuts, soybeans, tree nuts, cow's milk, eggs, crustacea, and fish (Taylor, 1992, *Food Technol.,* 148-152; Sampson, 1992. *Food Technol.,* 141-144; and Burks, 1992, *Food Allergy News,* 2:(1) 1). The frequency of food allergy is highest in infancy and early childhood, and decreases with increasing age (Collin-Williams and Levy, 1984, Allergy to food other than milk. In Food intolerance, R. K. Chandra, ed., pp. 137-186. Elsevier, N.Y.). About 5% of children younger than three and 1.5% of the general population experience food allergy disorders, or about 4 million Americans suffer from food allergies (Sampson, 1997, *JAMA* 1997, 278 (22): 1888-1894).

Food allergies are increasing worldwide, and peanut is one of the most allergenic food products. It is estimated that over 600,000 children in the United States have peanut allergies. While childhood allergies to egg and cow's milk may disappear, allergies to nuts, peanuts, soybeans, fish and shellfish tend to persist for the lifetime of the individual (Bock, 1982. *J. Allergy Clin. Immunol.,* 69:173-177; Collin-Williams and Levy, 1984, supra).

Hypersensitive responses to peanut allergens can be fatal. Contact with the slightest amount of peanut protein can be life threatening to particularly sensitive individuals. There is little data on the incidence of near-fatal and fatal allergic reactions to food, but peanut has been documented as a top offender (Taylor, 1987, *Nutritional Toxicol.* 2: 173-177; Yunginger et al., 1988, *JAMA* 260:(10) 1450-1452; Evans et al., 1988, *CMAJ,* 139: (8) 231-232.; Burks et al. 1992; Bock 1992, *J. Allergy Clin. Immunol.,* 90:683-685). It is reported that approximately 125 people die each year in the USA of food-induced anaphylaxis (Burks et al., 1999, *Arch Allergy Immunol,* 119 (3):165-172.)

The allergy can show up at the first exposure to peanuts, often before the age of three. Most people develop peanut allergies early in life, and few ever grow out of peanut allergies, even in adulthood. Allergic reactions to peanuts are often acute and severe (Sampson, 1990. Peanut anaphylaxis. *J. Allergy Clin. Immunol.* 86:1-3). The most common manifestation of peanut allergy is acute hives (or urticaria) following exposure. However, some patients may rapidly develop severe angiodema, swelling of the face, bronchospasm and anaphylaxis, following exposure. Some individuals are so sensitive that they will develop symptoms if they kiss someone who has eaten peanuts or if they eat out of a food utensil that has been in contact with peanuts.

Peanut (*Arachis hypogaea*), a crop grown worldwide, is an annual plant belonging to the family Leguminosae, native to South America, and is commercially grown in the southeastern regions of the United States, specifically in Alabama, Florida, Georgia, North Carolina, and Virginia, and in many other countries of the world. In the United States, several types are grown, although the three most popular peanut types are the Virginia, Spanish, and runner varieties. Virginia peanuts are used primarily for whole kernel consumption and confections. Runner types are used most frequently for oil production and peanut butter (Woodroof, 1983. In: *Peanuts: Production, Processing, Products*, Woodroof, Ed., Westport, Conn.). Most of the peanut crop in the United States is used for the production of peanut butter. The most widely cultivated peanut cultivars in the USA are 'Florunner', 'New Mexico Valencia', 'Georgia Green', and 'Georgia Red'.

Although information about the nature and identity of allergenic components of foods is quite limited, it is known that food allergens are most often proteins (Nordlee, et al., 1981., *J. Allergy Clin. Immunol.,* 68:376-383), and provoke an abnormal immunoglobulin E-(IgE) mediated immunological reaction. Several allergenic peanut proteins have been isolated, identified, characterized and classified as minor or major allergens. (Burks A W, Williams L W, Helm R M, Connaughton C, Cockrell G, O'Brien T., *J Allergy Clin Immunol* 1991; 88:172-179; Burks A W, Cockrell G, Connaughton C, Helm R M.; *J Allergy Clin Immunol* 1994; 93:743-750; Gleeson P A, Jermyn M A., *J Plant Physiol* 1977; 4, 25; Kleber-Janke T, Crameri R, Appenzeller U, Becker W M, Schlaak M., *Int Arch Allergy Immunol* 1999; 119:265-274; Rabjohn P, Helm E M, Stanley J, West C M, Sampson H, Burks A W, Bannon G A., *J Clin Invest* 1999; 103(4):535-542; Sachs M I, Jones R T, Yunginger J W., *J Allergy Clin Immunol* 1981; 67(1):27-34; Stanley J S., www.ncbi.nlm.nih.gov/htbin . . . ery?uid=1236995, 1996)

These proteins include glycoproteins, arachin, conarachin, peanut agglutinin and peanut phospholipase. Of these peanut protein allergens, six were classified as major allergens, with an estimated molecular weights of 44, 40, 33, 21, 20, and 18 kDa (De Jong et al., 1998, *Clin. Exp. Allergy,* 28: 743-751).

Burks et al. 1992 (*J. Allergy Clin. Immunol.* 90: 962-969) identified two major peanut allergens, designated Ara h 1 and Ara h 2, which are glycoproteins with isoelectric points and molecular weights of 4.55 and 63,500 Daltons and 5.2 and 17,000 Daltons, respectively. These peanut allergens are stable at a temperature of up to 100° C., at pH conditions between pH 2.8 and pH 10, and resistant to digestion by acid and digestive enzymes. Peanut, peanut butter, and peanut flour retain their allergenicity through processing, and crude peanut oil may also be contaminated with these proteins.

The allergens Ara h1 and Ara h2 are found in the cotyledon of peanut, and both are recognized by more than 90% of peanut-sensitive patients, establishing them as major allergens. Ara h1 has been isolated and a cDNA clone produced and sequenced, making this the first peanut allergen to be sequenced (Burks, et al., 1996, *J. Clin. Invest.* 96, 1715-1721). The partial cDNA sequences of Ara h2 (Stanley et al., 1997, *Arch. Biochem. and Biophys*, 342:244-253), Ara h3 (Rabjohn, et al., 1999, *J. Clin. Invest.* 103:535-542), Ara h4, Ara h6, and Ara h7 (Kleber-Janke, et al., 1999, *Int. Arch. Allergy Immunol.*, 119:265-274) have also been recently cloned and sequenced.

Currently, no treatment exists for food allergies. Administration of epinephrine and antihistamines is used to reverse the symptoms of food-allergic reactions. Thus, the most effective management strategy in the prevention of peanut allergies is complete avoidance of peanut-containing foods (Schmidl, et al., 1994, Food Technol. 10:77-85). However, this is difficult to do, as it requires diligent reading of labels and ingredient listings.

The peanut is a popular and important food, and provides a cheap source of protein and oil for human and animal consumption. Peanuts provide niacin, magnesium, Vitamin C, manganese and chromium in significant amounts and smaller amounts of potassium, Vitamin B6, folic acid, phosphorus, copper and biotin. Furthermore, peanut is widely used in both western and oriental cooking, and is added to a variety of foods such as pastries, sandwiches, egg rolls, chili, syrups, flours, sauces, and confections (Nordlee et al., 1981; Yunginger et al., 1988; Evans et al., 1988; Burks et al., 1991). Because dining out is prevalent in the current American lifestyle, the social stigma associated with refraining from taking part in restaurant or party meals by allergic individuals because of the potential threat for accidentally ingesting peanut, makes the strict avoidance of peanut unlikely and unrealistic (Heiner and Navin, 1975, *J. Allergy Clin. Immunology* 55:82). For example, one of Britain's most promising young athletes died in June 1999, after suffering a seizure triggered by an accidental ingestion of peanut while eating a chicken sandwich (The Independent-London-Jun. 21, 1999).

An investigation of a wide variety of commercially grown peanuts showed no naturally occurring allergen-free peanut lines. (Dodo H W, Marsic D, Mallender M, Cebert E, Viquez O M. Submitted to *J. Allergy Clin. Immunology*, 2000).

Therefore, there is a need for an alternative solution for the allergic individual. Specifically, there is a need for allergen-free peanut plants, peanuts, and peanut products.

There is also a need for purified peanut allergen proteins which will enable the production of allergen-specific antibodies for detection of allergen in food products, and for prophylaxis and treatment of allergic reactions to peanut.

Modern tools of molecular biology have the potential to offer new transgenic allergen-free peanuts to the peanut-allergic population and the peanut industry. Therefore, an understanding of the molecular structure and regulatory features of the genes is needed to provide needed information for gene silencing and production of allergen-free peanut seeds.

SUMMARY OF THE INVENTION

The present invention provides an isolated polynucleotide molecule comprising a peanut allergen antisense gene, and/or sense gene, or fragment thereof, operably linked to a promoter and a terminator, the promoter and terminator functioning in a peanut cell. In particular, there is provided an isolated polynucleotide molecule comprising the Ara h2 peanut allergen antisense gene together with its structural and regulatory features. Furthermore, there is provided a polynucleotide molecule comprising an antisense gene that codes for an RNA molecule that is complementary to, the mRNA molecule coded for by a peanut allergen protein gene selected from the group consisting of Ara h1, Ara h2, Ara h3, Ara h4, Ara h5, Ara h6, and Ara h7, and any other peanut allergen gene that can induce an allergic reaction in humans.

The present invention further provides the isolated nucleotide sequences of the antisense genes. Seed-preferred promoters, particularly a constitutive promoter, an inducible promoter and a tissue-preferred promoter, are operably linked to the antisense genes, and/or sense genes.

The invention also provides modified transformation vectors such as pCB13, pB1426, pBI436, comprising a polynucleotide molecule having peanut allergen antisense genes, and/or a sense genes, or fragments thereof, operably linked to a promoter and a terminator, the promoter and terminator functioning in a peanut cell.

Yet further provided is a transformed bacterium containing a polynucleotide molecule comprising a peanut allergen antisense gene, and/or a sense gene or fragments thereof, operably linked to a promoter and a terminator, the promoter and terminator functioning in a peanut cell.

The invention also provides a peanut plant cell containing a polynucleotide molecule comprising a peanut allergen antisense gene, and/or a sense gene, or fragment thereof, operably linked to a promoter and a terminator, the promoter and terminator functioning in a peanut cell. Still further provided is a peanut plant containing a cell comprising the polynucleotide molecule having a peanut allergen antisense gene, and/or a sense gene, or fragment thereof, operably linked to a promoter and a terminator, the promoter and terminator functioning in a peanut cell. Yet further, the invention provides a seed produced by the peanut plant containing a cell comprising the polynucleotide molecule having a peanut allergen antisense gene, and/or a sense gene, or fragment thereof, operably linked to a promoter and a terminator, the promoter and terminator functioning in a peanut cell.

The present invention provides methods for producing a transgenic peanut plant with reduced or undetectable allergen protein content in the seed, comprising transforming a recipient peanut plant cell with a DNA construct comprising a peanut allergen antisense gene, and/or a sense gene, or fragment thereof, regenerating a peanut plant from the recipient cell which has been transformed with the DNA construct, and identifying a fertile transgenic peanut that produces seeds having reduced or undetectable or undetectable allergen protein content. The recipient peanut plant cell may be transformed by biolistic or *Agrobacterium*-mediated methods.

There is also provided a method wherein the recipient peanut plant cell is transformed with a DNA construct comprising an antisense gene, and/or a sense gene, having a nucleotide sequence based on the Ara h1, Ara h2, Ara h3, Ara h4, Ara h6, or Ara h7 genes, or any other allergen genes. Yet further is provided a method wherein the recipient peanut cell is transformed with a DNA construct comprising more than one antisense gene, and/or sense genes.

The invention further provides a method for producing a transgenic peanut plant with reduced or undetectable allergen protein content in the seed, comprising transforming a recipient peanut plant cell with a DNA construct comprising a peanut allergen gene, or fragment thereof, regenerating a peanut plant from the recipient cell which has been transformed the DNA construct, and identifying a fertile transgenic peanut that produces seeds having reduced or undetectable allergen protein content. Still further, the invention provides a method wherein the recipient peanut plant cell is transformed with the polynucleotide by the biolistic method. Yet further, the invention provides a method wherein the recipient peanut plant cell is transformed with the polynucleotide by the *Agrobacterium*-mediated method.

Also provided is a method wherein the recipient peanut plant cell is transformed with a DNA construct comprising a peanut allergen gene, or fragment thereof, that is the Ara h1, Ara h2, Ara h3, Ara h4, Ara h5, Ara h6, Ara h7 or any other peanut allergen gene. The invention further provides a method wherein the recipient peanut cell is transformed with a DNA construct comprising more than one peanut allergen gene.

Also provided is a method wherein homologous sequence region between two or more peanut allergen genes is used to down-regulate peanut allergens. A method is provided for producing a transgenic peanut plant with reduced or undetectable allergen protein content in the seed comprising the steps of identifying a homologous region common to more than one Ara h allergen gene; cloning the homologous region in a vector wherein the homologous region is operably linked to a promoter; transforming a recombinant peanut cell with the vector; and identifying a regenerated fertile transgenic peanut plant that produces seed having reduced or undetectable allergen protein content.

BRIEF DESCRIPTION OF THE DRAWINGS

FIG. 2 shows the nucleotide and deduced amino acid sequences (SEQ ID NOS 1-2, respectively) of peanut allergen Ara h2 gene. The figure also shows a putative TATA box, an ATG initiation codon, the first stop codon (TGA), and putative polyadenylation signal (bold). Six additional stop codons are underlined. The deduced polypeptide encoded by the open reading frame has 207 amino acids residues and includes a putative signal peptide of 21 amino acid residues (underlined).

FIG. 3 shows the PCR amplified region (in capital letters) of Ara h2 genomic DNA (SEQ ID NO: 3), cloned in transformation vectors (pUC18 and pBI434) in sense and antisense orientations to down-regulate Ara h2, Ara h6, and Ara h7 allergens in peanut. This region is a portion of the sequence homology region between Ara h2, Ara h6, and Ara h7 allergens.

FIG. 4 shows the PCR amplified region (in capital letters) of Ara h3 cDNA (SEQ ID NO: 4), cloned in transformation vectors (pUC18 and pBI434) in sense and antisense orientations to down-regulate Ara h3, and Ara h4 allergens in peanut. This region is a portion of the sequence homology region between Ara h3 and Ara h4 allergens.

FIG. 5 shows PCR amplified region (in capital letters) of Ara h1 P41B cDNA (SEQ ID NO: 5), cloned in transformation vectors (pUC18 and pBI434) in sense and antisense orientations to down-regulate Ara h1 P41 B, and Ara h 1 P17 allergens in peanut. This region is a portion of the sequence homology region between Ara h1 P41B and Ara h1 P17 allergens.

FIG. 6 is a schematic representation of plasmid constructs to down-regulate peanut allergens in transgenic peanuts.

FIG. 7 shows the PCR amplified region of Ara h5 cDNA (SEQ ID NO: 6) (shown in bold), cloned in sense and antisense orientations in transformation vectors (pUC18 and pBI434), to down-regulate Ara h5 allergen in peanut.

FIG. 9 shows the nucleotide sequence (residues 1-154 of SEQ ID NO:1) of the Ara h2 promoter upstream of the ATG initiation codon.

DEFINITIONS

Figure 1:
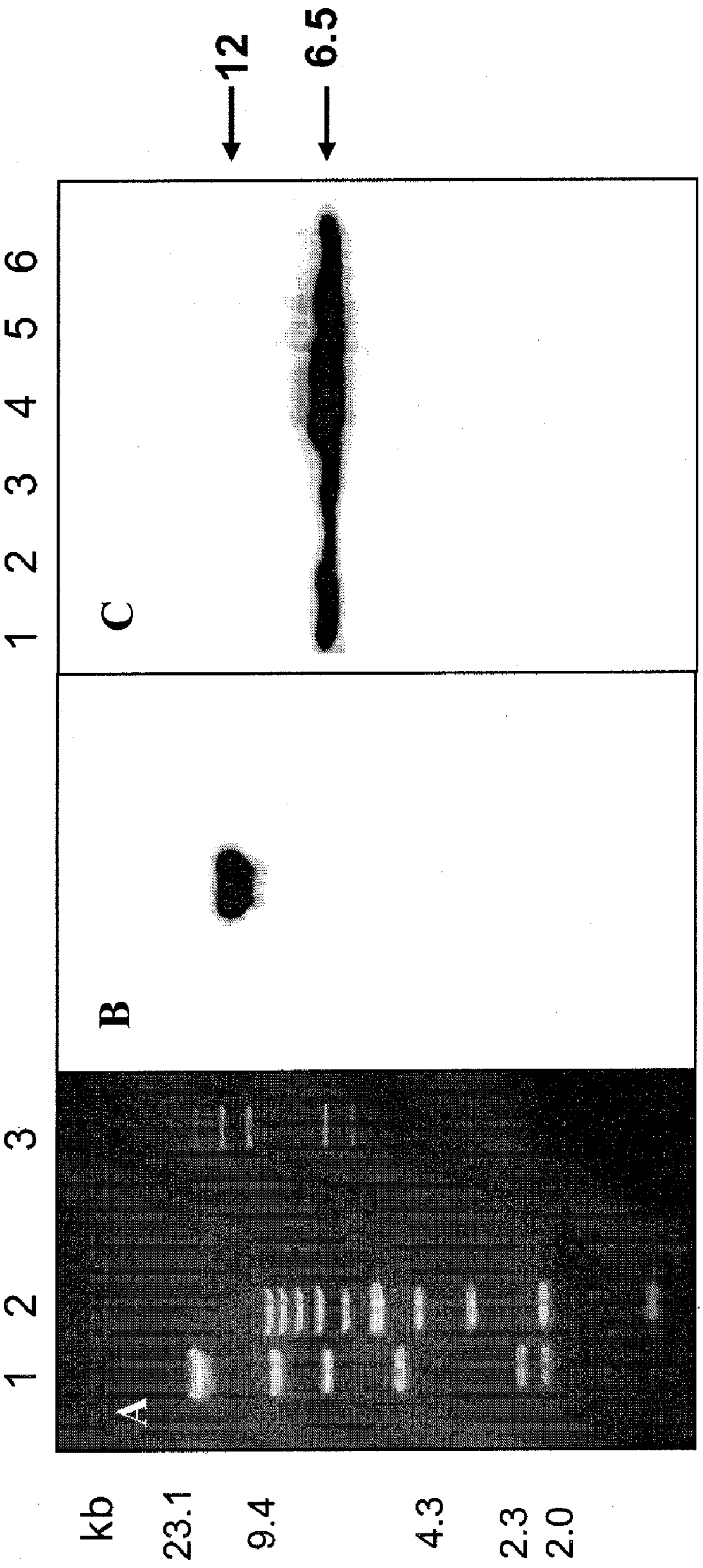
FIG. 1 shows a Southern hybridization of (A) the Bam HI digestion pattern of the positive 50 kb lambda clone for Ara h2 gene (lane 3), Lambda DNA/Hind III markers (lane 1), 1 kb DNA step ladder (lane 2); (B) hybridization of an 80-mer labeled probe with a subcloned 12 kb Bam HI-fragment; and (C) hybridization of an 62-mer labeled probe with a subcloned 6.5 Bam HI-fragment (clones 1-6).

As used herein, the term gene should be understood to be a full-length DNA sequence encoding a protein or an RNA molecule, as well as a truncated fragment thereof A gene can be naturally occurring or synthetic.

Marker gene should be understood as a gene encoding a selectable marker (e.g., encoding antibiotic resistance) or a screenable marker (e.g., encoding a gene product which permits detection or transformed cells or plants). The marker gene for the polynucleotide molecule of the present invention can be any nucleotide sequence which codes for a protein or polypeptide which allows transformed cells to be distinguished from non-transformed cells. The marker gene can be, for example, a herbicide resistance gene, an antibiotic resistance gene, a β-glucuronidase (GUS) gene, or a luciferase gene.

A promoter is a nucleotide sequence upstream from the transcriptional initiation site and which contains all the regulatory regions required for transcription. Examples of promoters suitable for use in DNA constructs of the present invention include viral, fungal, bacterial, animal and plant-derived promoters capable of functioning in plant cells. The promoter may be selected from so-called constitutive promoters or inducible promoters. If a promoter is an inducible promoter, then the rate of transcription increases in response to an inducing agent. In contrast, the rate of transcription is not regulated or largely unregulated by an inducing agent, if the promoter is a constitutive promoter.

Examples of suitable inducible or developmentally regulated promoters include the napin storage protein gene (induced during seed development), the malate synthase gene (induced during seedling germination), the small sub-unit RUBISCO gene (induced in photosynthetic tissue in response to light), the patatin gene (highly expressed in potato tubers) and the like. Examples of suitable constitutive promoters include the cauliflower mosaic virus 35S (CaMV 35S) and 19S (CaMV 19S) promoters, the nopaline synthase promoter, octopine synthase promoter, heat shock 80 (hsp 80) promoter and the like. It will be appreciated that the promoter employed in the present invention should be strong enough to control the transcription of a sufficient amount of an antisense RNA molecule to cause an inhibition of expression of a peanut allergen in transformed cells.

A tissue-preferred promoter is a DNA sequence that, when operably linked to a gene, directs a higher level of transcription of that gene in a specific tissue than in some or all other tissues in an organism. Examples of such promoters are a stem-specific promoter such as the AdoMet-synthetase promoter (Peleman et al., 1989, *The Plant Cell* 1:81-93), a tuber-specific promoter (Rocha-Sosa et al., 1989, *EMBO J.* 8:23-

29). For example, a seed-preferred promoter is a DNA sequence that directs a higher level of transcription of an associated gene in plant seeds. Examples of seed-preferred promoters include the seed specific promoter of the USP gene of *Vicia faber* (U.S. Pat. No. 5,917,127); the 7S protein promoter of soybean (Bray et al., 1987, *Planta* 172:364-370) and the 2S promoter (Krebbers et al., 1988, *Plant Physiol.* 87:859-866).

A terminator is a DNA sequence at the end of a transcribed unit which signals termination of transcription. These elements are 3'-non-transcribed sequences containing polyadenylation signals which act to cause the addition of polyadenylate sequences to the 3' end of primary transcripts. Examples of terminators particularly suitable for use in nucleotide sequences and DNA constructs of the invention include the nopaline synthase polyadenylation signal of *Agrobacterium tumefaciens*, the 35S polyadenylation signal of CaMV, octopine synthase polyadenylation signal and the zein polyadenylation signal from *Zea mays*.

An isolated nucleic acid molecule is a fragment of nucleic acid molecule that has been separated from the nucleic acid of an organism or other natural environment of the nucleic acid an isolated nucleic acid molecule includes a chemically-synthesized nucleic acid molecule. Other examples of isolated nucleic acid molecule include in vivo or in vitro transcripts of the nucleic acids of the present invention.

Isolated polypeptides are polypeptides not in their naturally occurring form or have been purified to remove at least some portion of cellular or non-cellular molecules with which the proteins are naturally associated. However, the "isolated" protein may be included in compositions containing other polypeptides for specific purposes, for example, as stabilizers, where the other polypeptides may occur naturally associated with at least one polypeptide of the present invention.

The terms "complementary" or "complementarity" refer to the capacity of purine and pyrimidine nucleotides to associate non-covalently to form partial or complete double stranded nucleic acid molecules. The following base pairs are naturally complementary: guanine (G) and cytosine (C); adenine (A) and thymine (T); and adenine (A) and uracil (U).

Complementary DNA (cDNA) is a single-stranded DNA molecule that is formed from a mRNA template by the enzyme reverse transcriptase. Typically, a primer complementary to portions of an mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides. In the case of an antisense gene, expression involves transcription of the antisense DNA into an antisense RNA molecule that is complementary to the sense mRNA.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that codes for the antisense RNA is termed an antisense gene. An antisense RNA molecule inhibits the expression of the gene to which it corresponds.

A vector is a DNA molecule, such as a plasmid, cosmid, viruses or bacteriophage, that has the capability of replicating autonomously in a host cell. Cloning vectors typically contain a marker gene and one or a small number of restriction endonuclease recognition sites for insertion of foreign DNA sequences without affecting the essential biological function of the vector.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" or "operatively linked to" the regulatory elements.

"Host cell" refers to any eukaryotic, prokaryotic, or other cell that is suitable for propagating or expressing an isolated nucleic acid that is introduced into the cell by any suitable means known in the art. The cell can be part of a tissue or organism, isolated in culture or in any other suitable form. A recombinant host may be any prokaryotic or eukaryotic cell that contains either a cloning vector or expression vector. This term also includes those prokaryotic or eukaryotic cells that have been genetically engineered to contain an isolated gene in the chromosome or genome of the host cell.

A transgenic peanut plant is a plant having one or more plant cells that contain a foreign gene. The foreign gene is usually non-native, meaning that it is originated from a source other than the host plant and does not share sequence homology to the host genome. The foreign gene may also be native, meaning that it has the nucleotide sequence found in the host. The transgenic plant is made by one of many transformation methods well-known in the art. As used herein, a fertile transgenic plant is capable of transmitting a foreign gene to its progeny of further descendants. As used herein, the term transformation refers to alteration of the genotype of a host plant by the introduction of native or non-native nucleic acid sequences into the genomes of the plant cell.

Peanut allergen variants, according to the invention, include DNA or protein molecules that resemble, structurally and functionally, the polynucleotide with the sequence of any peanut allergen gene. Peanut allergen genes that can be used for the present invention include Ara h1, Ara h2, Ara h3, Ara h4 Ara h5, Ara h6, Ara h7, and any other such genes that are identified and cloned which induce an allergic response in a human.

Hybridizing peanut allergen variants: Nucleic Acid variants within the invention also may be described by reference to their physical properties in hybridization. One skilled in the field will recognize that nucleic acid can be used to identify its complement or homologue, using nucleic acid hybridization techniques. It will also be recognized that hybridization can occur with less than 100% complementarity. However, given appropriate choice of conditions, hybridization techniques can be used to differentiate among DNA sequences based on their structural relatedness to a particular probe. For guidance regarding such conditions see, for example, Sambrook et al., 1989, *Molecular Cloning—A Laboratory Manual,* 2nd ed., Vol. 1-3; and Ausubel et al., 1989, *Current Protocols in Molecular Biology, Green Publishing Associates and Wiley Interscience, N.Y.*

Structural relatedness between two polynucleotide sequences can be expressed as a function of "stringency" of the conditions under which the two sequences will hybridize with one another. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences (Bolton et al., 1962, *Proc. Natl. Acad. Sci.* 48:1390.

Hybridization stringency is thus a function of many factors, including overall DNA concentration, ionic strength, temperature, probe size and the presence of agents that disrupt hydrogen bonding. Factors promoting hybridization include high DNA concentrations, high ionic strengths, low temperatures, longer probe size and the absence of agents that disrupt hydrogen bonding.

Hybridization usually is done in two stages. First, in the "binding" stage, the probe is bound to the target under conditions favoring hybridization. A representative hybridization solution comprises 6×SSC, 0.5% SDS, 5×Denhardt's solution and 100 μg of non-specific carrier DNA. See Ausubel et al., supra, section 2.9, supplement 27 (1994). A stock 20×SSC solution contains 3M sodium chloride, 0.3M sodium citrate, pH 7.0. Of course many different, yet functionally equivalent, buffer conditions are known. For high stringency, the temperature is between about 65° C. and 70° C. in a hybridization solution of 6×SSC, 0.5% SDS, 5×Denhardt's solution and 100 μg of non-specific carrier DNA. Moderate stringency is between at least about 40° C. to less than about 65° C. in the same hybridization solution. In both cases, the preferred probe is 100 bases.

Second, the excess probe is removed by washing, which is most important in determining relatedness via hybridization. Washing solutions typically contain lower salt concentrations. A medium stringency wash solution contains the equivalent in ionic strength of 2×SSC and 0.5-0.1% SDS. A high stringency wash solution contains the equivalent in ionic strength of less than about 0.2×SSC and 0.1% SDS, with a preferred stringent solution containing about 0.1×SSC and 0.1% SDS. The temperatures associated with various stringencies are the same as discussed above for "binding." The washing solution also typically is replaced a number of times during washing. For example, typical high stringency washing conditions comprise washing with 2×SSC plus 0.05% SDS five times at room temperature, and then washing with 0.1×SSC plus 0.1% SDS at 68° C. for 1 h. Blots containing the hybridized, labeled probe are exposed to film for one to three days.

Particularly preferred molecules are at least 75% of the length of those molecules.

Structural variants may also be due to substitutions, insertions, additions, and deletions. With regard to amino acid sequence, "substitutions" generally refer to alterations in the amino acid sequence that do not change the overall length of the polypeptide, but only alter one or more amino acid residues, substituting one for another in the common sense of the word. "Insertions," unlike substitutions, alter the overall length of the polypeptide. Insertions add extra amino acids to the interior (not the amino- or carboxyl-terminal ends) of the subject polypeptide. "Deletions" diminish the overall size of the polypeptide by removal of amino acids from the interior or either end of the polypeptide. Preferred deletions remove less than about 30% of the size of the subject molecule. "Additions," like insertions, also add to the overall size of the protein. However, instead of being made within the molecule, they are made on the N- or C-terminus of the encoded protein. Unlike deletions, additions are not very size-dependent. Indeed, additions may be of virtually any size. Preferred additions, however, do not exceed about 100% of the size of the native molecule. The artisan understands "additions" also to encompass adducts to the amino acids of the native molecule.

In general, both the DNA and protein molecules of the invention can be defined with reference to sequence identity. As used herein, "sequence identity" refers to a comparison made between two molecules using standard algorithms well-known in the art. Although any sequence algorithm can be used to define "sequence identity," for clarity, the present invention defines identity with reference to the Smith-Waterman algorithm, where the open reading frame of a gene is used as the reference sequence to define the percentage identity of polynucleotide homologues over its length. When "sequence identity" is used with reference to a polypeptide, the entire polypeptide having the sequence of a polypeptide of interest is used as a reference sequence to determine the percent identity of polypeptide homologues over its length.

Preferred polynucleotides are those having at least about 80% sequence identity to the open reading frame. Particularly preferred polynucleotides have at least about 90% sequence identity. Even more preferred polynucleotides have at least about 95% sequence identity, and most preferred polynucleotides have at least 98% sequence identity. As used herein, two nucleic acid molecules or proteins are said to "share significant sequence identity" if the two contain regions that possess greater than 85% sequence (amino acid or nucleic acid) identity.

DETAILED DESCRIPTION OF THE PREFERRED EMBODIMENT

1. Overview

The present invention discloses the isolated, sequenced and characterized genomic clone of the major peanut allergen gene Ara h 2. The present invention also provides an isolated polynucleotide molecule comprising the coding sequence for each of the peanut allergen genes operably linked to a promoter and a terminator, the promoter and terminator functioning in a peanut cell. The isolated peanut allergen gene, or fragment thereof, is operably linked to a selected promoter and transformed into peanut cells to make a stably transformed plant.

Peanut seeds comprising multiple copies of a peanut allergen gene exhibit reduced or undetectable allergen protein content due to cosuppression, antisense RNAs, or double-stranded RNAs by combining sense and antisense genes. The selected promoter may be a constitutive or tissue-preferred promoter such as a seed-preferred promoter. Peanut plants may be transformed with more than one peanut allergen gene, or fragment of each gene, in order to produce peanut seeds containing reduced or undetectable quantities of more than one peanut allergen proteins. Alternatively, peanut plants may be transformed with a DNA construct comprising more than one peanut allergen gene, or fragment of each gene, in order to produce peanut plants and seeds containing reduced or undetectable quantities of more than one peanut allergen proteins.

Furthermore, the peanut plants may be transformed with a DNA construct comprising one or more polynucleotide sequences found in more than one peanut allergen gene in a process to produce peanut plants and seeds containing reduced or undetectable quantities of several different peanut allergen proteins. In a preferred embodiment, the peanut allergen gene is selected from the group consisting of Ara h1, Ara h2, Ara h3, Ara h4, Ara h5, Ara h6, and Ara h7, and any other peanut allergen gene, and fragments thereof.

The invention also provides an isolated polynucleotide molecule comprising a peanut allergen antisense gene, and/or a sense gene, and/or combined antisense and sense genes, operably linked to a promoter and a terminator, the promoter and terminator functioning in a peanut cell. The isolated peanut allergen antisense gene, and/or sense gene, and/or combined antisense and sense genes, or fragment thereof, is operably linked to a selected promoter and transformed into peanut cells to make a stably transformed plant. Peanut seeds comprising a peanut allergen gene exhibit reduced or undetectable allergen protein content. The selected promoter may be a constitutive or tissue-preferred promoter such as a seed-preferred promoter.

Peanut plants may be transformed with more than one peanut allergen antisense gene, and/or sense gene, and/or combined antisense and sense genes, or fragment of each gene, in order to produce peanut plants and seeds containing reduced or undetectable quantities of several different peanut allergen proteins. Alternatively, peanut plants may be transformed with a polynucleotide comprising more than one peanut allergen antisense genes, or fragments thereof, in a process to produce peanut plants and seeds containing reduced or undetectable quantities of several different peanut allergen proteins. Furthermore, the peanut plants may be transformed with a DNA construct comprising one or more antisense genes comprising a polynucleotide sequence that is complementary to a DNA sequence found in more than one peanut allergen gene in a process to produce peanut plants and seeds containing reduced or undetectable quantities of several different peanut allergen proteins.

Peanut plants may be transformed with a DNA construct comprising one or more sense genes, comprising a polynucleotide sequence that is similar to a DNA sequence found in more than one peanut allergen genes in a process to produce peanut plants and seeds containing reduced or undetectable quantities of several different peanut allergen proteins.

In a preferred embodiment, the peanut allergen antisense gene generates an RNA molecule which is complementary to a sense mRNA molecule encoding a peanut major allergen protein selected from the group consisting of Ara h1, Ara h2, Ara h3, Ara h4, Ara h5, Ara h6, Ara h7, and any other allergen gene, and fragments thereof. The peanut allergen sense gene generates an RNA molecule which is identical to a sense mRNA molecule encoding a peanut major allergen protein selected from the group consisting of Ara h1, Ara h2, Ara h3, Ara h4, Ara h5, Ara h6, Ara h7, and any other allergen gene, and fragments thereof. A combination of a peanut allergen antisense gene and sense gene generates a simultaneous expression of sense and antisense sequences corresponding to a peanut major allergen protein selected from the group consisting of Ara h1, Ara h2, Ara h3, Ara h4, Ara h5, Ara h6, Ara h7, and any other allergen gene, and fragments thereof.

Also provided is a vector, a bacterium, and a peanut plant cell comprising the polynucleotide molecules of the invention. Still further provided is a method for producing a transgenic peanut plant with reduced or undetectable allergen content. The method comprises a) preparing the polynucleotide molecules of the instant invention; b) transforming a recipient peanut plant cell with the polynucleotide molecules of the instant invention; c) regenerating a peanut plant from the recipient cell which has been transformed with the polynucleotide molecule; and d) identifying a fertile, transgenic peanut plant comprising the polynucleotide molecule and reduced or undetectable allergen content. A preferred embodiment of the method utilizes a biolistic apparatus or a *Agrobacterium* Ti plasmid for the transformation of the peanut plant cell. The polynucleotide molecules of the instant invention include peanut allergen genes, peanut allergen antisense genes, peanut allergen sense genes, and a combination of peanut allergen antisense and sense genes, and fragments thereof.

The present invention also provides methods for testing for allergens in transgenic peanuts using ELIZA.

The present invention also provides methods, utilizing traditional plant breeding procedures, for incorporating the allergen-free peanut germplasm into diverse peanut genetic backgrounds.

2. Peanut Allergen Genes

Peanut contains multiple allergens. An allergen is defined as a molecule that elicits an abnormal immunoglobulin E (IgE)-mediated immunological reaction within certain individuals. Burks et al., 1992, *J. Allergy Clin. Immunol.,* 90: 962-969, identified two glycoproteins which are major peanut allergens, Ara h1 and Ara h2, with molecular weight and isoelectric points of 63.5 kDa and 4.55 and 17 kDa and 5.2 respectively. De Jong et al., 1998 *Clin. Exp. Allergy,* 28 (6): 743-751, identified and classified six peanut proteins as major allergens with an estimated molecular weight of 44, 40, 33, 21, 20, and 18 kDa. Rabjohn et al., 1999, *J. Clin. Invest.* 103(4): 535-542, isolated another peanut allergen Ara h3 Kleber-Janke et al., 1999, *Int. Arch. Allergy Immunol.* 119: 265-274, identified and cloned Ara h4, Ara h5, Ara h5, Ara h6 and Ara h7 by Kleber-Janke T., et al., 1999.

The nucleotide sequences of the published Ara clones can be obtained as follows: Arah1, Clone P41B (SEQ ID NO: 12—GenBank Accession number L34402), Burks W, Cockrell, Stanley S T, Helm R M and Bannon G A (1995), *Clin. Invest* 96: 1715-1721; Arah1 Clone P17 (SEQ ID NO: 13—GenBank Accession number L38853), Burks W, Cockrell, Stanley S T, Helm R M and Bannon, Unpublished; Arah2 cDNA (GenBank Accession number L77197), Stanley J S, Unpublished; Arah2 genomic DNA, Viquez O M, Summer C G and DODO W H (2000), *The Journal of Allergy and Clinical Immunology* 107:713-717; Arah3 cDNA (partial coding sequence: SEQ ID NO: 14—GenBank Accession number AF093541), Robinson P, Helm E M, Stanley S J, West C M, Sampson H A, Burk A W and Banorm G A (1998) Unpublshed; Arah4 cDNA (SEQ ID NO: 15—GenBank Accession number AF086821), Kleber-Janke T, Crameri R, Appenzeller U, Schlaak M, and Becker W M (1999), *Int Arch. Allergy Immunol* 119 (4) 265-274; Arah5 cDNA (SEQ ID NO: 16—GenBank Accession number AF059616), Kleber-Janke T, Crameri R, Appenzeller U, Schlaak M, and Becker W M (1999), *Int Arch. Allergy Immunol* 119 (4) 265-274; Arah6 cDNA (partial coding sequence: SEQ ID NO: 17—GenBank Accession number AF092846), Kleber Janke T, Crameri R, Appenzeller U, Schlaak M, and Becker W M (1999), *Int Arch. Allergy Immunol* 119 (4) 265-274; Arah7 cDNA (SEQ ID NO: 18—GenBank Accession number AF091737), Kleber-Janke T, Crameri R, Appenzeller U, Schlaak M, and Becker W M (1999), *Int Arch. Allergy Immunol* 119 (4) 265-274.

3. Isolation of Genes Encoding Peanut Allergen Proteins

Several different methods are available for isolating genes coding for peanut allergen proteins. Most approaches begin with the purification of the protein. The purified protein is then subjected to amino acid microsequencing, either directly or after limited cleavage. The partial amino acid sequence that is obtained can be used to design degenerate oligonucleotide probes or primers for use in the generation of unique, nondegenerate nucleotide sequences by polymerase chain reaction (PCR), sequences that can in turn be used as probes for screening genomic DNA libraries. Antibodies raised against purified protein may also be used to isolate DNA clones from expression libraries.

Alternatively, the sequences of DNA coding for related proteins may be used as starting points in a cloning strategy, so-called "cloning by homology". Another way of utilizing sequence information from different species is to take advantage of shorter areas of high sequence homology among related DNAs from different species and to perform PCR to obtain "species-specific" nondegenerate nucleotide sequences. Such a sequence can then be used for library screening or even for direct PCR-based cloning. Detection of the desired DNA can also involve the use of PCR using novel primers.

Libraries are screened with appropriate probes designed to identify the genomic DNA of interest. For expression libraries (which express the protein), suitable probes include monoclonal or polyclonal antibodies that recognize and specifically bind to the peanut allergen protein. Screening the genomic DNA library with the selected probe may be accomplished as described in the example below.

Screening genomic DNA libraries using synthetic, degenerate oligonucleotides based on partial amino acid sequences, or oligonucleotides based on 5' cDNA sequences, or oligonucleotides based on homologous regions between several allergens of purified known peanut allergen proteins as probes, are the preferred methods of this invention.

The oligonucleotide sequences selected as probes should be of sufficient length and sufficiently unambiguous to minimize false positives. The design of actual nucleotide sequence(s) of the probe(s) is based on regions of the peanut allergen protein that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled according to procedures well known in the art, such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

4. Construction of Nucleic Acids

The isolated nucleic acids of the present invention can be made using (a) standard recombinant methods, (b) synthetic techniques, (c) purification techniques, or combinations thereof, as are well known to those skilled in the art. The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. Additional sequences that may be inserted include adapters or linkers for cloning and/or expression. Use of cloning vectors, expression vectors, adapters, and linkers is equally well known to those skilled in the art.

The various restriction enzymes disclosed and described herein are commercially and/or available and the manner of use of the enzymes including reaction conditions, cofactors, and other requirements for activity are well known to one of ordinary skill in the art (New England BioLabs, Boston; Life Technologies, Rockville, Md.). Reaction conditions for particular enzymes are preferably carried out according to the manufacturer's recommendation.

A variety of cross-linking agents, alkylating agents and radical generating species as pendant groups on polynucleotides of the present invention can be used to bind, label, detect, and/or cleave nucleic acids using methods and reagents known in the art.

i) Recombinant Methods for Constructing Nucleic Acids

The isolated nucleic acid compositions of this invention can be obtained from biological sources using any number of cloning methodologies known to those of skill in the art. Oligonucleotide probes that selectively hybridize to the polynucleotides of the present invention may be used to identify the desired sequence in a cDNA or genomic DNA library. Isolation of RNA and construction of cDNA and genomic libraries is well known to those of ordinary skill in the art.

ii) Synthetic Methods for Constructing Nucleic Acids

The isolated nucleic acids of the present invention can also be prepared by direct chemical synthesis using the solid phase phosphoramidite triester method (Beaucage and Caruthers, *Tetra. Letts.* 22(20): 1859-1862 (1981)); an automated synthesizer (VanDevanter et al., *Nucleic Acids Res.,* 12: 6159-6168 (1984)); or the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

iii) Recombinant Expression Cassettes

The present invention further provides recombinant expression cassettes comprising a peanut allergen gene, peanut allergen antisense gene, or a peanut sense gene, or a combination of peanut allergen antisense and sense genes, or fragments thereof, operably linked to transcriptional initiation regulatory sequences that will direct the transcription of the polynucleotide in the intended host cell. Both heterologous and endogenous (native) promoters can be employed to direct expression. These promoters can also be used, for example, in recombinant expression cassettes to drive expression of antisense, sense or a combination of antisense and sense nucleic acids, to reduce or to eliminate peanut allergen content in a desired tissue.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution. Suitable promoters include the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiation (AUG) at the beginning and a termination codon (UAA, UGA or UAG) appropriately positioned at the end of the polypeptide to be translated.

The polynucleotides can optionally be joined to a vector containing a selectable marker for propagation in a host. Such markers include, e.g., dihydrofolate reductase or neomycin resistance for eukaryotic cell culture and tetracycline, ampicillin or kanamycin resistance genes for culturing in *E. coli* and other bacteria. Representative examples of appropriate hosts include, but are not limited to, bacterial cells, such as *E. coli, Streptomyces* and *Salmonella typhimurium* cells; and fungal cells, such as yeast cells.

5. Control of Peanut Allergen Gene Expression

The present invention discloses methods to reduce or eliminate the expression of peanut allergen genes on the basis of antisense, co-suppression, dsRNA technology, and ribozymes.

Plant transformation technologies utilize molecular strategies to down-regulate or to inhibit the expression of endogenous plant genes. These proven strategies have been used to make the allergen-free-peanut plants of the instant invention. They include the antisense RNA strategy, homology dependent gene silencing (HDGS), and the double-stranded RNA method.

In the antisense RNA strategy (reviewed by Watson C F, and Don Grierson (1992), Antisense RNA in Transgenic Plants, fundamentals and applications. Hiatt Ed. p 255-281), it is considered that an antisense transcript suppresses gene expression post-transcriptionally by inhibiting RNA processing, transport from the nucleus, and translation, by hybridization with the sense molecules.

Matzke M A, and Matzke A T M (*Plant Physiol.* (1995), 107: 679-685), reviewed the mechanisms involved in homology dependent-gene silencing (HDGS). Double-stranded RNA (dsRNA) is a new tool to suppress gene expression in a number of organisms (Fire et al., 1998 Nature 391:806-811; Montgomery et al., 1998 *Proc. Natl. Acad. Sci.* 95:15502-15507; Kennerdell and Carthew, 1998 *Cell* 95:1017-1026, Misquitta and Paterson, 1999, *Proc. Natl. Acad. Sci.* 96:1451-1426, Ngo et al., 1998, *Proc. Natl. Acad. Sci.* 95:14687-14692) including plants (Waterhouse et al., 1998, *Proc. Natl. Acad. Sci.* 95:13959-13964). Double-stranded RNA has a very high specificity in suppressing the expression of the gene from which the dsRNA sequence is derived without detectable effect on the expression of genes unrelated in sequence (Fire et al., 1998, Nature 391:806-811). The molecular mechanisms by which dsRNA generates gene silencing are not well understood yet. It is however speculated that, the gene silencing is a result of a cellular defense to dsRNA formation from nuclear transcripts.

Two classes of HDGS are distinguished by their effect on transcription on the target gene. Examples of transcriptional gene silencing (TGS) are known in which the phenomenon of DNA methylation is the key factor. The promoter of the target gene is methylated, and thereby, becomes inactive. (Brusslan A J, Karlin-Neumann G A, Huang Lu and Tobin M E (1993), *The Plant Cell* 5: 667-677; Neuhuber F, Park Y D, Matzke A J M, Matzke M A, (1994) *Molecular and General Genetics* 244: 230-241) When a transgene integrates into a heavily methylated chromosomal region, it is rapidly silenced. By DNA-DNA interactions, a transgene locus that is silenced can lead to silencing of homologous genes. When the silenced locus is methylated the target locus also becomes methylated.

Double-stranded DNA blocks the activity of genes by artificially providing sense and antisense RNA corresponding to the target gene. Gene silencing by dsRNA is a post-transcriptional process (PTGS). It is demonstrated that triggering of PTGS by direct introduction of foreign RNA requires that both the sense and the antisense strands are provided exogenously, even if a cell already has substantial pool of naturally synthesized sense and antisense RNAs from distinct chromosomal sites, to produce a PTGS response (Ngo et al., 1998; Fire et al., 1998; Waterhouse et al., 1998;) All three strategies, antisense RNA, co-suppression and double-stranded RNA are used in the present invention.

Antisense technology is a versatile approach for controlling expression of endogenous cellular genes and extinguishing cellular gene expression. The principle is to introduce into a cell an RNA or a single stranded DNA molecule complementary to the mRNA of the target gene (the "antisense molecule"). The antisense molecule can base-pair with the naturally occurring corresponding cellular mRNA and prevent its translation. The protocol was originally developed for the control of the gene encoding polygalacturonase during fruit ripening in tomato (Smith et al. 1988, *Nature* 334:724-726). Considerable effort has been devoted to the development of antisense RNA technology for the production of novel plant mutants which have the advantage of being stably inherited (Schuch, 1991, *Soc. Exp. Biol.* 117-127).

Antisense technology, however, has not been applied to peanut. Prior to this invention, there has not been peanut plants or germplasm, whether naturally occurring or genetically engineered, that is partially or completely allergen free. In fact, in an ELISA screen of 32 commercial peanut cultivars by the inventors of the instant invention, no allergen-free cultivar was identified, although a significant difference in allergen level was found among the cultivars.

The present invention provides a nucleotide sequence which is an antisense gene encoding an antisense RNA molecule which has a nucleotide sequence complementary to a sense mRNA molecule that codes for a major peanut allergen protein. This antisense gene is under transcriptional control of a promoter and a terminator, both promoter and terminator capable of functioning in peanut plant cells.

The antisense gene can be of any length provided that the antisense RNA molecule encoded by the antisense gene is sufficiently long to form a complex with a sense mRNA molecule encoding a peanut allergen protein. For the purposes of the description of the present invention, the antisense gene can be from about 50 nucleotides in length up to a length which is equivalent to the full length of the gene. Preferably, the length of the DNA encoding the antisense RNA will be from 100 to 1500 nucleotides. The preferred gene of the present invention is a DNA that codes for an RNA having substantial sequence identity or similarity to the mRNA encoding a peanut allergen protein. Thus the antisense DNA of the present invention may be selected from the group of peanut allergen genes or fragments thereof.

The antisense, sense and the combination of antisense and sense peanut allergen genes may consist of a plurality of subsequences, wherein each subsequence codes for an antisense RNA molecule, a sense RNA molecule and a dsRNA molecule directed to a different peanut allergen gene or a different portion of the same peanut allergen gene. Naturally, the skilled artisan will appreciate that the subsequences can be adjacent to one another, or noncontiguous, in any order. The invention also provides for a nucleotide sequence that is a variant of the antisense genes described herein.

The present invention discloses a DNA construct comprising the nucleotide sequence according to the invention, as well as a modified transformation vectors comprising the sequence or construct. The vector may be a plasmid or virus. The vector may be the Ti plasmid of *Agrobacterium tumefa-*

*ciens*. The vector advantageously carries a selectable marker gene. The nucleotide sequence of the invention may code for an mRNA which comprises, in the 5' to 3' direction, (i) a promoter, (ii) at least one peanut allergen antisense gene, and (iii) a terminator. In the DNA construct shown in FIG. 6., the Arah2 gene is expressed from its native promoter, and the marker genes are operably linked to the CaMV35s promoter.

Conserved sequences from different allergen genes may be used to down-regulate all known and/or existing allergens (Arah1, Arah2, Arah3, Arah4, Arah5, Arah6, Arah7, and any other allergens) in peanut plants. Suppression of expression of more than one allergen gene may be done by introducing multiple copies of a gene or gene fragment into a construct, using sense or antisense homologous regions. The resultant construct contains more than one homologous antisense or sense gene fused in frame and may be used to reduce or eliminate expression of more than one target allergen gene.

Suitable transformation vectors such as pUC 18, pBI426 and modified versions of pBI426 (shown in FIG. 8) are used for carrying out biolistic transformation. Modified versions of pBI434 (Dalta et al., 1991), (also shown in FIG. 8), a binary vector for transformation using *Agrobacterium tumefaciens* (FIG. 6). (See Example 3, below) Transformation vectors carry the transgenes, flanked by a promoter such as the Arah2 promoter, or the 35S promoter, and the nopaline synthase terminator. The peanut allergen gene may be portions of the open reading frame (ORF) of peanut allergens Arah1, Arah2, Arah3, Arah4, Arah5, Arah6, Arah7, or any other allergen gene.

Different types of transformation cassettes are made to down-regulate peanut allergens. Regions of homology between the nucleotide sequences of different allergens are PCR amplified from the genomic DNA of Arah2. The PCR product is cloned in both antisense and sense orientation into the same transformation vector to produce dsRNA in transformed peanut cells. Or, the antisense construct is used in co-transformation with the construct to produce dsRNA in transformed peanut cells. Another alternative, is to synthesize at least 100 base pair oligonucleotides corresponding to the homology region between the above three allergens to make the antisense and sense transgene constructs.

For control of allergen genes Arah3, and Arah4, it is noted that cDNA sequences of these two allergens have 95% homology, shown in capital letters in the sequence in FIG. 4. A portion of two hundred base pairs within the homology region is PCR amplified, and then cloned into the above transformation vectors in sense, or antisense orientation. Alternatively, polynucleotides based on the Arah3 and Arah4 homologous region may be used for allergen gene control, such as synthesis of 100 base pair oligonucleotides within the region of homology and synthesis of at least 100 base pair oligonucleotides at the 5' end of the cDNA. These oligonucleotides are used in the same way as the PCR products.

Other polynucleotides are also used to down-regulate Arah1. Two different Arah1 clones (Arah1 P41B, and Arah1 P17) were identified in peanut (Burk et al, 1995). The cDNA sequences of these two clones show 96% homology, as highlighted by capital letters in the sequence shown in FIG. 5. A portion of at least two hundred base pairs within the homology region is PCR amplified, and then cloned into transformation vectors in sense, and antisense orientations. Other polynucleotides that can be used to regulate Arah1 expression include 100 base pair oligonucleotides within the region of homology, and 100 or more base pair oligonucleotides at the 5' end of the cDNA of each clone.

The Ara h5 cDNA sequence does not have any homology with other peanut allergens. FIG. 7. shows the PCR amplified region for the antisense and sense constructs (shown in bold in the sequence) to down-regulate Arah5 proteins in peanut plants.

6. Transgenic Peanut Plants

The allergen-free peanut seed according to the present invention may be produced in essentially any of the various transformation methods known to those skilled in the art of plant molecular biology. (See, for example, Wu and Grossman, (Eds.) 1987*, Methods of Enzymology*, Vol. 153, Academic Press, incorporated herein by reference). As used herein, the term "transformation" refers to alteration of the genotype of a host plant by the introduction of non-native or native nucleic acid sequences. Particle bombardment of embryogenic callus, or *agrobacterium* transformation, are the methods of choice for production of transgenic monocotyledonous plants, but has found widespread application for transformation of dicotyledonous plants as well. (Vasil, 1994*, Plant Mol. Biol.* 25, 925-937). In many cases transformed plant cells may be cultured to regenerate whole plants which can subsequently reproduce to give successive generations of genetically modified plants.

Experiments have shown that foreign genes can be transferred to peanut using *Agrobacterium* mediated transformation (Lacorte et al., 1991*, Plant Cell Reports* 10:354-357. Cheng et al., 1991*, Proc. Amer. Peanut Res. Educ. Soc.,* 23:30.) or microprojectile bombardment (Cheng et al., 1991, supra; Ozias-Akins et al., 1993*, Plant Science* 93:185-194). The microprojectile bombardment protocol was reported to produce stably transformed peanut plants.

To commence a transformation process in accordance with the present invention, it is first necessary to construct a suitably modified vector and properly introduce the vector into the plant cell. The details of the construction of the vectors utilized herein are known to those skilled in the art of plant genetic engineering.

For example, the allergen-antisense containing constructs utilized in the present invention can be introduced into plant cells using Ti plasmids, root-inducing (Ri) plasmids, and plant virus vectors. For reviews of such techniques see, for example, Weissbach & Weissbach, 1988*, Methods for Plant Molecular Biology*, Academic Press, N.Y., Section VIII, pp. 421-463; and Grierson & Corey, 1988, Plant Molecular Biology, 2d Ed., Blackie, London, Ch. 7-9, and Florsch et al., *Science* 227:1229 (1985), incorporated herein by reference.

One of skill in the art will be able to select an appropriate vector for introducing the nucleic acid sequences of the invention in a relatively intact state. Thus, any vector which will produce a plant carrying the introduced DNA sequence should be sufficient. Even a naked piece of DNA is expected to be able to confer the properties of this invention, though at low efficiency. The selection of the vector, or whether to use a vector, is typically guided by the method of transformation selected.

For example, a heterologous nucleic acid sequence can be introduced into a plant cell utilizing *Agrobacterium tumefaciens* containing the Ti plasmid. When using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, *Biotechnol.,* 1:262, 1983; Hoekema et al., 1983*, Nature* 303: 179.) Such a binary system is preferred because it does not require integration into Ti plasmid in *Agrobacterium.*

Methods involving the use of *Agrobacterium* include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium.*

In addition, gene transfer can be accomplished by in situ transformation by *Agrobacterium*, as described by Bechtold et al., 1993*, C. R. Acad. Sci. Paris* 316:1194. This approach is based on the vacuum infiltration of a suspension of *Agrobacterium* cells.

Alternatively, the allergen antisense gene-containing construct described herein can be introduced into a plant cell by contacting the plant cell using mechanical or chemical means. For example, nucleic acid can be mechanically transferred by direct microinjection into plant cells utilizing micropipettes. Moreover, the nucleic acid may be transferred into plant cells using polyethylene glycol which forms a precipitation complex with genetic material that is taken up by the cell.

The nucleic acid can also be introduced into plant cells by electroporation (Fromm et al., *Proc. Natl. Acad. Sci., U.S.A.* 82:5824 (1985), which is incorporated herein by reference). In this technique, plant protoplasts are electroplated in the presence of vectors or nucleic acids containing the relevant nucleic acid sequences. Electrical impulses of high field strength reversibly permeabilize plant membranes allowing the introduction of nucleic acids. Electroporated plant protoplasts reform the cell wall, divide and form a plant callus. Selection of the transformed plant cells with the transformed gene can be accomplished using phenotypic markers as described herein above.

Another method for introducing nucleic acid into a plant cell is high velocity biolistic penetration by small particles with the nucleic acid to be introduced contained either within the matrix of small beads or particles, or on the surface thereof (Klein et al., 1987, Nature 327:70. Although, typically only a single introduction of a new nucleic acid sequence is required, this method particularly provides for multiple introductions.

Cauliflower mosaic virus (CaMV) may also be used as a vector for introducing heterologous nucleic acid into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid may be recloned and further modified by introduction of the desired nucleic acid sequence. The modified viral portion of the recombinant plasmid is then excised from the parent bacterial plasmid, and used to inoculate the plant cells or plants. Plasmids pCB13, pBI426, and pBI434 may also be used as vectors for introducing heterologous nucleic acids into plants. Peanut allergen genes are cloned into these vectors in sense or antisense orientation for single transformations or multiple transformations (co-bombardments). (Chen et al., 1998 *Nature Biotechnology* 16: 1060-1064; Pawloski, Somers et al., 1996 *Mol Biotechnol* 6:17-30) Using *Agrobacterium* Ti vector-mediated plant transformation methodology, all polynucleotide molecules of this invention can be inserted into peanut genomes after the polynucleotide molecules have been placed between the T-DNA border repeats of suitable disarmed Ti-plasmid vectors (Deblaere, R. et al., 1987, *Methods in Enzymology* 153 277-292). This transformation can be carried out in a conventional manner, for example as described in EP 0116718, PCT publication WO 84/02913 and EPA 87400544.0. The polynucleotide molecule can also be in non-specific plasmid vectors which can be used for direct gene transfer (e.g. de la Pena, A., 1987*, Nature,* 325:274-276).

As indicated above, the polynucleotide molecule according to the instant invention preferably encodes antisense RNAs to all peanut allergen genes, including Ara h1, Ara h2, Ara h3, Ara h4, Ara h5, Ara h6, Ara h7, and any other peanut allergen genes.

Alternatively, the skilled person will appreciate that nucleotide sequences as defined herein may be introduced into a peanut cell genome which already comprises one or more antisense, or sense, or a combination of sense and antisense allergen genes. Specifically, the polynucleotide molecule may contain the sequence encoding one of the antisense RNAs, the sense RNA, and sequential transformation (retransformation) may be used to introduce a second polynucleotide molecule comprising a different sense or antisense allergen gene. In this case, an alternative system to select transformants is needed for the second round of transformation. For example, two different selectable marker genes are used in the two consecutive transformation steps. The first marker is used for selection of transformed cells in the first transformation, while the second marker is used for selection of transformants in the second round of transformation. Sequential transformation steps using kanamycin and hygromycin have been described, for example by Sandler et al. (1988) and Delauney et al. (1988). This retransformation leads to the combined expression of two sense or antisense genes, or some combination thereof, resulting in a transgenic plant that is free of or has reduced or undetectable expression of, more than one allergen. This transformation step can be repeated until all known peanut allergen genes have been silenced and the resulted transgenic peanut plant is completely free of known existing allergens.

Another alternative is to transform a peanut plant using a polynucleotide molecule containing a sequence encoding one antisense RNA, or one sense RNA, and/or a combination of antisense and sense RNA, and transform another peanut plant using a second polynucleotide molecule containing a sequence encoding the other antisense RNA, sense RNA, and/or a combination of antisense and sense RNA, in a single plant genome through crosses of the two independently transformed peanut plants. It is well-known to a skilled person that the plants, prior to crossing, should be rendered homozygous regarding the transgene through selfing. The first plant should be a plant transformed with a first antisense RNA or a sense RNA, and/or a combination of antisense and sense RNA, or an F1 plant derived thereof through selfing. Selection methods can be applied to the plants obtained from this cross in order to select those plants having the two antisense RNAs genes, sense RNA genes, and/or a combination of antisense and sense RNA genes present in their genome (e.g. by Southern blotting) and blocking the expression of one or more allergens (e.g. by separate ELISA detection). A skilled artisan would recognize that this strategy can be repeated, such that further antisense genes, sense genes, and/or a combination of antisense and sense genes, are introduced sequentially by crossing.

7. Allergen-Free Transgenic Peanut: Method to Render the Antisense Transgene Homologous, and Use of Allergen Free Peanut in Traditional Breeding Programs Allergen-free germplasm may be incorporated in traditional breeding programs for incorporation of this novel trait into desirable peanut genotypes. Methods for producing novel, allergen-free peanut hybrids using the transgenic allergen-free peanut plant of the present invention are known in the art. Each of the following references is incorporated in its entirety, herein, by reference: Moore, 1989, K. M. et al., *J. Heredity* 80(3): 252; Norden, A. J., Peanuts, Culture and Uses. *Am. Peanut Res. and Educ. Soc.*, Stillwater, Okla. (C. T. Wilson ed. 1973); Norden, A. J. in *Hybridization of Crop Plants* (H. H. Hadley ed. 1980); Norden, A. J., et al., Breeding of the cultivated peanut in *Peanut Science and Technology*, (H. E. Pattee ed. 1992); Norden, A. J. et al. Florida Agr. Res. 3:16-18 (1984).

Initially, a homozygous line containing the antisense allergen gene can be obtained, following conventional peanut breeding by self-pollination for a number of generations. This homozygous line may be introgressed into diverse peanut backgrounds in the same, or different market classes by breeding methods known in the art, such as successive selection and inbreeding.

The allergen-free peanut germplasm of the present invention can be introgressed into diverse peanut backgrounds in the same, or different market classes, for example, the runner-type market class (*A. hypogaea* subsp. *hypogaea* var. *hypogaea* botanical type Virginia) as well as the Virginia (*A. hypogaea* subsp. *hypogaea* var. *hypogaea* botanical type Virginia), Peruvian (*A. hypogaea* subsp. *hypogaea* var. *hypogaea* botanical type Peruvian runner), Valencia (*A. hypogaea* subsp. *fastigata* var. *fastigata* botanical type Valencia) and Spanish (*A. hypogaea* subsp. *fastigata* var. *vulgaris* botanical type Spanish) market classes. Peanuts in the runner-type market class are the most commonly used varieties and are found in diverse products such as peanut butter, salted nuts and confectionery products. On the other hand, peanut varieties in the Virginia market class are largely used as salted nuts and in-shell market. The Valencia is largely used in peanut butter while the Spanish type is used in certain niche markets where small round peanuts are needed such as confectionery products and red skin peanuts. Finally, the Peruvian runner market class is grown in certain regions of Mexico.

The allergen-free peanut germplasm of the present invention is introgressed into different peanut backgrounds by conventional methods well know to the skilled artisan in the field of peanut breeding. More specifically, crosses are made according to methods described by Norden, A. J., Peanuts, Culture and Uses, supra. Am. Peanut Res. and Educ. Soc., Stillwater, Okla. (C. T. Wilson ed. 1973); Norden, A. J. in *Hybridization of Crop Plants* (H. H. Hadley ed. 1980); Norden, A. J., et al., Breeding of the cultivated peanut in *Peanut Science and Technology*, (H. E. Pattee ed. 1992); Norden, A. J. et al. *Florida Agr. Res.* 3:16-18 (1984), the entirety of each is incorporated by reference. Introgression of the allergen-free characteristic is via the traditional plant breeding cross pollination techniques.

Allergen-free peanut plants may be propagated by planting homozygous seeds and harvesting the crop.

8. Production of Foods Using Allergen-Free Peanut

Allergen free peanuts produced according to the instant invention are processed and manufactured into food products using methods well known to a skilled artisan. Allergen-free peanut products are produced using the same standard food processing methods, processing equipment and sanitation practices, as those used in the production of their non-allergen-free counterparts. A skilled artisan would recognize that managing the risk of cross contamination in a food plant producing allergen-free peanut products is critical. If possible the system should be dedicated to producing only allergen-free foods (Beckman and Coult, 1999, *Food Testing & Analysis* 5 (3): 15-17).

9. Protein Expression

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Polypeptides of the invention can also include an initial modified methionine residue, in some cases as a result of host-mediated processes.

Purified proteins of the present invention may be used in the treatment of individuals allergic to peanut allergens, for example, via percutaneous specific hyposensitization therapy (see, e.g. Kaneko et al., U.S. Pat. No. 5,951,984) or via oral hyposensitization therapy (Wells et al., 1991, *J. Infect. Dis.,* 8:66; Trentham et al., 1993, *Science,* 261:1727; Weiner, et al., 1993, *Science,* 259:1321).

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., 1983, *Gene* 22: 229-235; Mosbach, et al., 1983, *Nature* 302: 543-545).

B. Expression in Eukaryotes

A variety of eukaryotic expression systems such as yeast, insect cell lines, plant and mammalian cells, are known to those of skill in the art. As explained briefly below, a of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., 1982, *Methods in Yeast Genetics*, Cold Spring Harbor Laboratory is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., 1986, *Immunol. Rev.* 89: 49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See Schneider, 1987, *J. Embryol. Exp. Morphol.* 27: 353-365.

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., 1983, *J. Virol.* 45: 773-781). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213-238 (1985).

A peanut allergen protein can be recovered and purified from recombinant cell cultures by well known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The monitoring of the purification process can be accomplished by Western blot techniques, radioimmunoassay, or other standard immunoassay techniques. These methods are described in many standard laboratory manuals, such as Sambrook, supra, Chapters 17.37-17.42; Ausubel, supra, Chapters 10, 12, 13, 16, 18 and 20.

10. Antibodies of the Invention

Antibodies raised against the proteins and protein fragments of the invention also are contemplated by the invention. In particular, the invention contemplates antibodies raised against the peanut allergen protein Ara h2, and variants thereof. Described below are antibody products and methods for producing antibodies capable of specifically recognizing one or more epitopes of the presently described proteins and their derivatives. Antibodies include, but are not limited to polyclonal antibodies, monoclonal antibodies (mAbs), humanized or chimeric antibodies, single chain antibodies including single chain Fv (scFv) fragments, Fab fragments, $F(ab')_2$ fragments, fragments produced by a Fab expression library, anti-idiotypic (anti-Id) antibodies, epitope-binding fragments, and humanized forms of any of the above.

As known to one in the art, these antibodies may be used, for example, in the detection of a target protein in a food sample. It is important for peanut-sensitive individuals to have a means of recognizing and avoiding peanut-containing products. Unfortunately, peanut allergens have been identified in non-peanut foodstuffs manufactured on common processing equipment that were inadequately cleaned. In general, Keating et al., 1990, *J. Allerg. Clin. Immunol.*, 86: 41-4, which is herein incorporated by reference, describes the use of a radioimmunoassay to detect peanut allergens in food processing materials and finished foods. In one embodiment, the allergen is covalently coupled to a solid phase. The allergen is reacted with a patient serum sample containing both allergen specific and non-specific IgE. The allergen reacts with the specific IgE in the patient sample. After washing away non-specific IgE, radioactively labeled antibodies against IgE are added forming a complex. Then unbound radioactively labeled anti-IgE is washed away. and the radioactivity of the bound complex is measured, for example, in a gamma counter. The more bound radioactivity found, the more specific IgE present in the sample. To classify the test results, patient counts are compared directly with counts of reference sera run in parallel. In another embodiment, the "two-site monoclonal antibody enzyme-linked immunosorbent assay" described in Burks et al. (U.S. Pat. No. 5,558,869) is used for the detection of the allergen.

The antibody of the present invention may also be utilized as part of treatment methods. For example, Saint-Remy et al., in U.S. Pat. No. 5,026,545 describes a method for treating allergic reaction via administering to a patient a mixture of allergen-antibody complex.

In general, techniques for preparing polyclonal and monoclonal antibodies as well as hybridomas capable of producing the desired antibody are well known in the art (Campbell, A. M., 1984, *Monoclonal Antibody Technology: Laboratory Techniques in Biochemistry and Molecular Biology*, Elsevier Science Publishers, Amsterdam, The Netherlands; St. Groth et al., 1980, *J. Immunol. Methods* 35:1-21; Kohler and Milstein, 1975, *Nature* 256:495-497), the trioma technique, the human B-cell hybridoma technique (Kozbor et al., 1983, *Immunology Today* 4:72; Cole et al., 1985, in *Monoclonal Antibodies and Cancer Therapy*, Alan R. Liss, Inc., pp. 77-96).

i) Polyclonal Antibodies

Polyclonal antibodies are heterogeneous populations of antibody molecules derived from the sera of animals immunized with an antigen, such as an inventive protein or an antigenic derivative thereof. Polyclonal antiserum, containing antibodies to heterogenous epitopes of a single protein, can be prepared by immunizing suitable animals with the expressed protein described above, which can be unmodified or modified, as known in the art, to enhance immunogenicity. Immunization methods include subcutaneous or intraperitoneal injection of the polypeptide.

Effective polyclonal antibody production is affected by many factors related both to the antigen and to the host species. For example, small molecules tend to be less immunogenic than other and may require the use of carriers and/or adjuvant. In addition, host animal response may vary with site of inoculation. Both inadequate or excessive doses of antigen may result in low titer antisera. In general, however, small doses (high ng to low μg levels) of antigen administered at multiple intradermal sites appears to be most reliable. Host animals may include but are not limited to rabbits, mice, and rats, to name but a few. An effective immunization protocol for rabbits can be found in Vaitukaitis, J. et al., 1971, *J. Clin. Endocrinol. Metab.* 33:988-991.

The protein immunogen may be modified or administered in an adjuvant in order to increase the protein's antigenicity. Methods of increasing the antigenicity of a protein are well known in the art and include, but are not limited to coupling the antigen with a heterologous protein (such as globulin β-galactosidase) or through the inclusion of an adjuvant during immunization. Adjuvants include Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Booster injections can be given at regular intervals, with at least one usually being required for optimal antibody production. The antiserum may be harvested when the antibody titer begins to fall. Titer may be determined semi-quantitatively, for example, by double immunodiffusion in agar against known concentrations of the antigen. See, for example, Ouchterlony et al., 1973, Chap. 19 in: *Handbook of Experimental Immunology*, Wier, ed, Blackwell. Plateau concentration of antibody is usually in the range of 0.1 to 0.2 mg/ml of serum (about 12 μM). The antiserum may be purified by affinity chromatography using the immobilized immunogen carried on a solid support. Such methods of affinity chromatography are well known in the art.

Affinity of the antisera for the antigen may be determined by preparing competitive binding curves, as described, for example, by Fisher, 1980, Chap. 42 in: *Manual of Clinical Immunology*, second edition, Rose and Friedman, eds., Amer. Soc. For Microbiology, Washington, D.C.

ii) Monoclonal Antibodies

Monoclonal antibodies (MAbs), are homogeneous populations of antibodies to a particular antigen. They may be obtained by any technique that provides for the production of antibody molecules by continuous cell lines in culture or in vivo. MAbs may be produced by making hybridomas, which are immortalized cells capable of secreting a specific monoclonal antibody.

Monoclonal antibodies to any of the proteins, peptides and epitopes thereof described herein can be prepared from murine hybridomas according to the classical method of Kohler, G. and Milstein, C., 1975, *Nature* 256:495-497; and U.S. Pat. No. 4,376,110 or modifications of the methods thereof, such as the human B-cell hybridoma technique (Kosbor et al., 1983, *Immunology Today* 4:72; Cole et al., 1983, *Proc. Natl. Acad. Sci. USA* 80: 2026-2030), and the EBV-hybridoma technique (Cole et al., 1985, Monoclonal antibodies and cancer therapy, Alan R. Liss, Inc., pp. 77-96).

In one method a mouse is repetitively inoculated with a few micrograms of the selected protein over a period of a few weeks. The mouse is then sacrificed, and the antibody producing cells of the spleen are isolated.

The spleen cells are fused, typically using polyethylene glycol, with mouse myeloma cells, such as SP2/0-Ag14 myeloma cells. The excess, unfused cells are destroyed by growth of the system on selective media comprising aminopterin (HAT media). The successfully fused cells are diluted, and aliquots are plated to microliter plates where growth is continued. Antibody-producing clones (hybridomas) are identified by detection of antibody in the supernatant fluid of the wells by immunoassay procedures. These include ELISA, as originally described by Engvall, 1980, *Meth. Enzymol.* 70:419, western blot analysis, radioimmunoassay (Lutz et al., 1988, *Exp. Cell Res.* 175:109-124) and modified methods thereof.

Selected positive clones can be expanded and their monoclonal antibody product harvested for use. Detailed procedures for monoclonal antibody production are described in Davis, L. et al. 1989, *Basic methods in molecular biology*, Elsevier, N.Y. Section 21-2. The hybridoma clones may be cultivated in vitro or in vivo, for instance as ascites. Production of high titers of mAbs in vivo makes this the presently preferred method of production. Alternatively, hybridoma culture in hollow fiber bioreactors provides a continuous high yield source of monoclonal antibodies.

The antibody class and subclass may be determined using procedures known in the art (Campbell, 1984, *Monoclonal Antibody Technology: Laboratory Techniques in Biochemistry and Molecular Biology*, Elsevier Science Publishers, Amsterdam, The Netherlands). MAbs may be of any immunoglobulin class including IgG, IgM, IgE, IgA, IgD and any subclass thereof. Methods of purifying monoclonal antibodies are well known in the art.

EXAMPLES

The following examples are given to illustrate the present invention. It should be understood that the invention is not to be limited to the specific conditions or details described in these examples. Throughout the specification, any and all references to publicly available documents are specifically incorporated by reference

Example 1

Isolation and Characterization of the Genomic Clones Encoding the Peanut Allergen Genes a) Library Screening To identify the genomic clone of the gene coding for the peanut allergen Ara hII, a peanut genomic library constructed in a Lambda Fix II vector (Stratagene Inc, La Jolla, Calif.) was screened with an 80 base pair oligonucleotide probe. The probe sequence (5'ctagtagccctcgcccttttcctc-ctcgctgcccacgcatctgcgaggcag-cagtgggaactccaaggagacagaagatg-3') (SEQ ID NO: 7) corresponds to nucleotide eleven to ninety-one of a published Ara h2 cDNA sequence (GeneBank accession L77197).

Twenty picomoles of the probe was end-labeled with radioactive adenosine 5'-triphosphate, tetra (triethylammonium), salt [gamma 32P] (32P) as described by Ausubel et al. (Ausubel F, Brent R, Kingston R E, Moore D D, Seidman J G, Smith J A, Struhl K. Short Protocols in Molecular Biology. 3rd ed.: John Wiley & Sons, Inc.; 1995) Fresh *Echerichia Coli* (*E. Coli*) VCS 257 (300 μL of 1×1010 cells/mL) were infected with 10 μL of the genomic library (1×103 pfu) for 30 minutes at 37° C. in a water bath. Then, 7 mL of top agarose (0.7%) at 47° C. were added, mixed and spread onto a pre-warmed (37° C.) 150 mm 2×LB agar plate. (Sambrook J, Fritsch E F, Maniatis T. Molecular Cloning: A Laboratory Manual. 2nd ed. New York: Cold Spring Harbor Laboratory Press; 1989) The plaques became visible after an overnight incubation at 37° C.

After plaque formation, the culture dishes were stored for 4 hours at 4° C., blotted on a piece of nylon membrane, denatured (NaOH, 0.5N) and neutralized (Tris-HCl, 1M) according to manufacturer's instructions (NEN Life Science Products, Inc., Boston, Mass.) and the DNA was crosslinked at 12,000 μjoules of UV energy for 45 seconds (UV Stratalinker 1800, Stratagene). Low stringency prehybridization (at 42° C. for 3 hours) and hybridization (at 42° C. overnight) were performed in the same solution containing 50% (v/v) formamide+10% (w/v) SDS+20% (w/v) dextran sulfate+1×Denhardt's solution+10 μg/mL salmon sperm DNA. During hybridization the labeled probe was added to the buffer. Membranes were washed with 2×SSC followed by 2×SSC+0.1% SDS for 15 minutes at room temperature, air dried, exposed to Kodak XAR-5-X ray film and developed after seven days at −80° C. Positive clones were matched with plaques on the Petri dishes, lifted and stored at 4° C. in 1 mL SM media containing a few drops of chloroform to prevent bacterial contamination. (Sambrook et al., supra) To confirm true positive clones, a second screening is performed as described above.

b) Purification of Putative Positive Clones

Selected putative positive clones were amplified as described by Sambrook et al. (Sambrook et al., supra) Lysate stocks of recombinant bacteriophage were prepared by infection of *E. coli* VCS 257 with each putative positive clone. The culture was grown for 6-8 hours at 37° C. and 300 rpm. Purification of lambda DNA was done using a Lambda kit (Qiagen Inc., Valencia Calif.) and the DNA was quantified using a fluorometer. (Hoefer Scientific Instruments. TKO 100DNA Mini Fluorometer Instruction Manual 1991)

c) Dot Blot Analysis

Positive clones were confirmed by dot blot analysis using a Bio-Dot SF Microfiltration apparatus (Bio-Rad Laboratories, Inc., Hercules, Calif.) and the Southern hybridization protocol. (Southern, E M., *J Mol Biol* 1975; 98(3): 503-517) One microgram of each purified DNA was blotted and transferred by capillary action to a nylon membrane. DNA was crosslinked to the membranes at 12,000 μjoules of UV energy for 45 seconds. The membrane was prehybridized at 50° C. for a least 4 hours in 6×SSPE+5×Denhardt's solution+0.05% (w/v) NaPyrPO4+0.5% (w/v) SDS+100 μg/mL salmon sperm DNA and hybridized at 50° C. overnight in 6×SSPE+1×Denhardt's solution+0.05% NaPyrPO4+0.5% SDS with the same 32P end-labeled probe used to screen the library. Stringent washes were performed at 50° C. for 15 minutes each in 6×SSPE+0.1% (w/v) SDS and 2×SSPE+0.1% (w/v) SDS. After air drying, the membrane was exposed to Kodak X-Omar AR film at −80° C. for two days and autoradiographed.

d) Subcloning

The selected positive lambda clone for Ara h2 was subcloned into a pBluescript II SK(+/−) phagemid vector (Stratagene, La Jolla, Calif.) to facilitate sequencing.

e) Subcloning of a 12 kb Fragment into a Phagemid Vector

The selected positive lambda clone was approximately 50 Kb with an insert fragment of about 16 Kb. The clone was digested with BamH I to release the insert and electrophoresed on a 0.7% agarose gel. Five fragments ranging in size from 5.5, 6.5, 9, 12 and 16 Kb were obtained. After Southern hybridization, only the 12 kb fragment hybridized to the 32P-labeled 80-mer probe. The 12 Kb fragment was then gel purified and subcloned into a pBluescript II SK+ plasmid vector (FIG. 1). Sequence analysis revealed that the selected 12 kb DNA fragment is truncated at a BamH I restriction site located about 212 nucleotides within the gene.

f) Subcloning of a 6.5 kb Fragment into a Phagemid Vector

A 62 base pair probe (5'-gtgcatgtgcgaggcattgcaacagat-catggagaaccagagcgataggttgcaggggaggc-3') (SEQ ID NO: 8) was designed from cDNA sequence downstream from the BamH I site to capture the remaining DNA fragment of the Ara hII gene. Of the five fragments obtained after digestion of the 50 kb lambda clone with BamH I, only the 6.5 kb fragment hybridized to this probe. This fragment was subcloned into pBluescript II SK+ plasmid vector and sequenced (FIG. 1).

g) Restriction Enzyme Digestion

For the BamH I digestion, the clone was electrophoresed on a 0.7% agarose gel. Five fragments ranging in size from 5.5, 6.5, 9, 12 and 16 Kb were obtained. After Southern hybridization, only the 12 kb fragment hybridized to the 32P-labeled 80-mer probe, and was then gel purified and subcloned into a pBluescript II SK+ plasmid vector (FIG. 1). Sequence analysis revealed that the selected 12 kb DNA fragment is truncated at a BamH I restriction site located about 212 nucleotides within the gene.

Restriction enzyme digestion with BamH I was performed at 37° C. Fragments were separated by electrophoresis on a 0.7% agarose gel, and five fragments, 5.5, 6.5, 9, 12 and 16 kb, were obtained. Each fragment was cut from the agarose gel and filtered through a Millipore Ultrafree®-DA filter (Millipore Corp., Bedford, Mass.) and precipitated in 100% ethanol. The digested pBluescript II vector was dephosphorylated with calf intestinal alkaline phosphatase prior to ligation with the DNA fragments, purified with an equal volume of phenol-chloroform, and precipitated in ethanol and resuspended in one volume of TE buffer (5 mM Tris (pH 7.5, 0.1 mM EDTA) to a final concentration of approximately 0.1 μg/μL.

h) Ligation

A 2:1 and 3:1 ratio of insert to vector DNA was selected. The ligation reaction was performed at 4° C. overnight then at room temperature for three hours. About 20 μL of ultra competent bacteria cells GENEHOGS™ Research Genetics (*E. coli* DH10B) were mixed with 1 μL of ligation mixture, electroporated and resuspended in 1 mL of 37° C. sterile SOC medium as described in the GENEHOGS™ protocol (Research Genetics, Huntsville, Ala.). Electroporation was performed using a Bio-Rad Gene Pulser electroporator (Bio-Rad Laboratories, Richmond, Calif.) with the following settings for a 1 mm gap electroporation cuvette (BTX™Genetronics, Inc, San Diego, Calif.): the field strength at 17 kV/cm, the resistor at 200Ω and the capacitor at 25 μF. Positive colonies were selected by blue-white color selection. (Stratagene Incorporation. Instruction manual: pBluescript®IIExo/Mug DNA Sequencing System. 1999) From each plate, white positive colonies containing a plasmid with an insert were picked and placed onto 6 mL of LB media supplemented with ampicillin (100 μg/mL) and incubated at 37° C. for 16 hours at 300 rpm. Plasmid DNA was purified using Qiagen Plasmid Purification kit, digested with BamH I and separated on 0.7% agarose gel to confirm the presence of a plasmid containing an Ara h2 insert.

i) Southern Hybridization

Digested DNA fragments were transferred onto a nylon membrane using an alkaline transfer protocol according to manufacturer instructions (Pall, NEN™ Life Science Products, Inc., Boston, Mass.). The DNA was crosslinked on the membrane as previously described and pre-hybridized at 65° C. for 3 hours in HyperHyb buffer (Research Genetics, Inc., Huntsville, Ala.). The probe was end labeled with 32P as described in the Fermentas kit (Fermentas Inc., Hanover, Md.), added to the hybridization solution and incubated at 65° C. for 3 hours in HyperHyb buffer. The membrane was washed three times at 65° C. for 15 minutes each in 0.1×SSC+0.1% SDS, rinsed once at room temperature in 1×SSC and exposed to x-ray film (Kodak, Biomax™ MS) at −80° C. for three hours and autoradiographed.

j) Sequencing

Purified positive p-Bluescript DNA (0.2 μg/μL) were sequenced with ABI PRISM™ Dye Terminator Cycle Sequencing Ready Reaction kit using AmpliTaq® DNA Polymerase, FS at Research Genetics, Inc. and the University of Alabama in Birmingham (UAB) using T3 and T7 sequencing primers.

k) Sequence Analysis

Approximately 1.2 kb of the peanut genomic DNA inner than been completely sequenced for both the sense and antisense strands, as can be seen in FIG. 2. It has been determined that Ara h2 is a gene family and contains iso-forms of the gene. Southern Blot analysis and the difference between the originally characterized cDNA clone and the characterization of the genomic clone of the present invention, is consistent with the existence of multiple genes.

Analysis of the sequence reveals a full length Ara h2 gene. Sequence analysis, comparison and homology searches are performed using the BLAST (Altschul S F, Madden T L, Schäffer A A, Zhang J, Zhang Z, Miller W, Lipman D J., *Nucl Acids Res* 1997; 25:3389-3402), and BLAST 2 sequences tools. (Tatusova T A, Madden T L., *FEMS Microbiol Lett* 1999; 174(2):247-250) Determination of leader sequence is done as described by Grierson and Covey. (Grierson D, Covey S N. Plant Molecular Biology. 2nd ed. New York (N.Y.): Chapman and Hall Publishers; 1988)

As evident from inspection of the sequence shown in FIG. 2, the open reading frame of the gene starts with a initiation codon (ATG) at position 1 and ends with a termination codon (TGA) at position 622. The predicted encoded protein is 207 amino acids long and includes a putative transit peptide of 21 residues.

One putative polyadenylation signal AATAAA is identified at position 951. Six additional putative stop codons are observed downstream of the first termination codon at positions 628 (TGA), 769 (TAA) 901 (TAA), 946 (TGA), 967 (TGA) and 982 (TGA). In the promoter region, 5' upstream of the start codon, a putative TATA box, TATTATTA is present at position −72. Comparison of the published cDNA and genomic sequences revealed the absence of an intron.

The location of the initiation codon ATG of Ara h2 is revealed for the first time. Until now only partial cDNA sequences have been published. (Stanley J S, King N, Burks A W, Huang S K, Sampson H, Cockrell G, Helm R M, West M, Bannon G A. *Arch Biochem Biophys* 1997; 342(2):244-253) The open reading frame of the genomic clone of Ara h2 is 621 nucleotides long while its cDNA (GeneBank accession L77197) is 492 nucleotides long. A comparison of the 2 sequences reveals that the cDNA sequence is 8 nucleotides short at the 5' region and does not include a start codon. In addition, the two sequences have complete identity from nucleotide 9 to 470 of the genomic clone. However, from nucleotide 471 they diverge with no homology downstream from this region at the nucleotide as well as the amino acid levels.

The termination codon is TGA at position 622. Not only is the termination codon usage different between the genomic (TGA) and the cDNA (TAA) clone but the later also ends 152 bp or 51 amino acids earlier than the genomic clone. Six additional stop codons are present in the 3' untranslated region at positions 628 (TGA), 769 (TAA), 901 (TAA), 946 (TGA), 967 (TGA) and 982 (TGA). It is known that some genes have several termination codons (Grierson & Covey, supra), however it is unclear which one is preferentially used. A gene usually undergoes post transcriptional and post translational modifications, which could explain some of the differences between the genomic and cDNA sequences.

A putative polyadenylation signal AATAAA is located at position 951 in the 3' untranslated region of the gene. This signal is identical to the consensus sequence for plants. Polyadenylation signals play key role in the stability and translation of the genetic message and direct the termination of transcription by RNA polymerase II (a functional polyadenylation signal and a downstream transcription 'pause' element are required for efficient pol II transcription termination in fission yeast. See Birse C, Proudfoot N., genome-www.stanford.edu/Saccharomyces/yeast96/f2021.html; Poly(A) signal controls both transcriptional termination and initiation between the tandem GAL10 and GAL7 genes of *Saccharomyces cerevisiae*. Greger I H, Proudfoot N J., *EMBO J.* 1998; 17(16):4771-4779).

FIG. 2 shows the deduced polypeptide encoded by the open reading frame which has 207 amino acids residues and includes a putative signal peptide of 21 amino acid residues (Nielsen H, Engelbrecht J, Brunak S, von Heijne G. *Protein Engineering* 1997, 10:1-6.). A signal peptide plays a role in the translocation of a protein from the cytosol to the target organelle within the cell. (Alberts B, Bray D, Lewis J, Raff M, Roberts K, Watson J D. Molecular Biology of the Cell. 3rd ed. New York (N.Y.): Garland Publishing, Inc; 1994) It is typically composed of hydrophobic amino acids such as tryptophan, phenylalanine, valine, leucine and isoleucine that have affinity for membranes of organelles. Ibid.

In the proximal region of the promoter, a putative TATA box TATTATTA is present at position −72 with respect to the initiation codon. The consensus signal for plant TATA boxes is TATAT/AA1-328. This is the most conserved sequence for RNA polymerase II-mediated transcription and is important for positioning the start of transcription. (Alberts et al. supra; Ellison K, Messing J., *Biotechnology* 1983; 12:115-139).

The 3' end of the Ara h2 gene (as shown in FIG. 2, downstream of the stop codon of the gene itself) can be fused, or operably linked, to a heterologous gene for expression of that gene.

Example 2

Construction Strategy of Peanut Allergen Gene Plasmids

Figure 8:
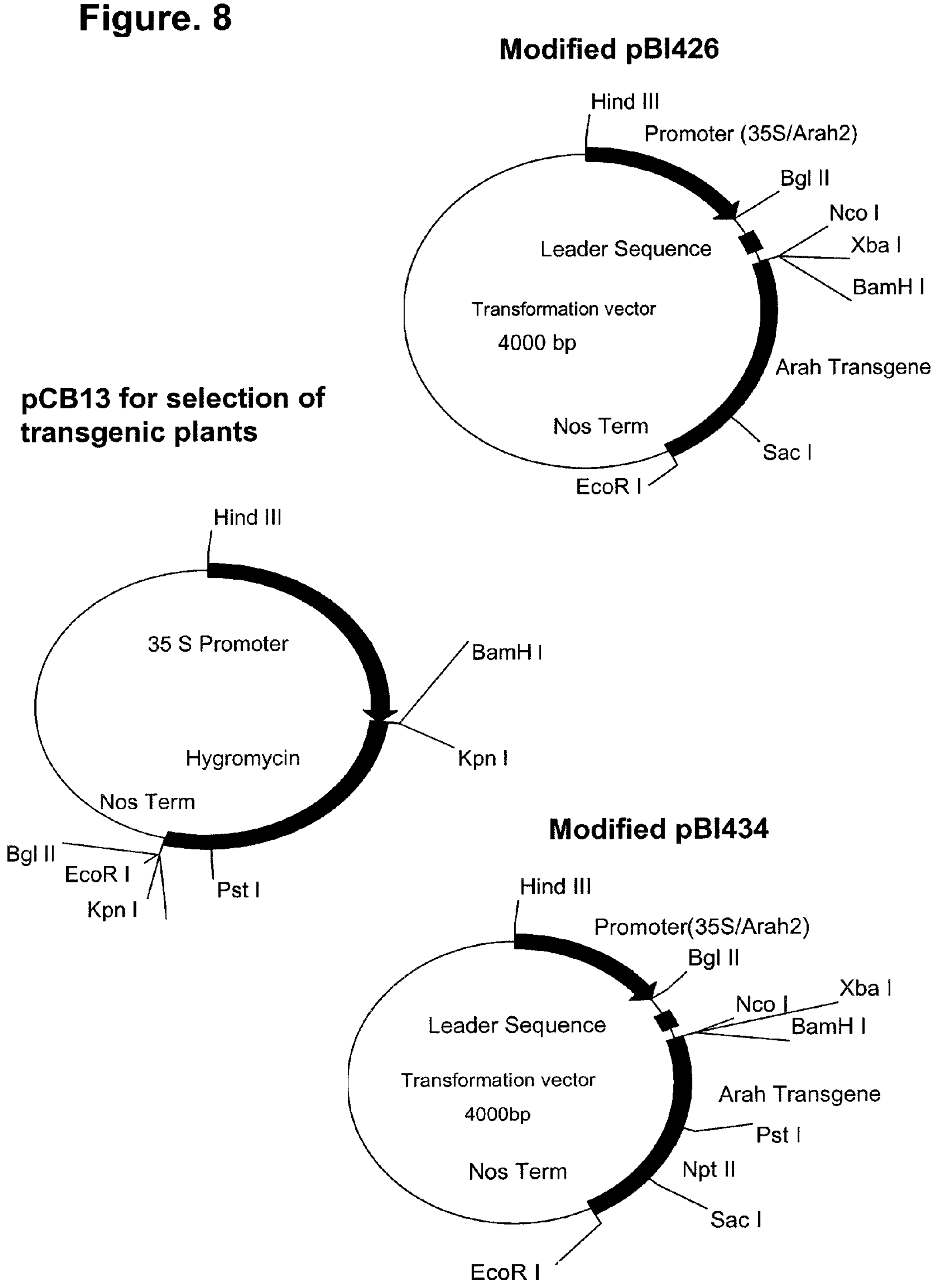
FIG. 8 shows diagrams of the plasmid constructs used in biolistic and *Agrobacterium*-mediated transformation of peanut.

Peanut allergen gene plasmids were constructed using expression cassettes containing antisense, and/or sense orientation of allergen genes linked to 35S/Ara h2 promoter and nos terminator, as shown in FIG. 8. Five types of constructs were used for the transformation of peanut tissue. The plasmid constructs pBI426, modified pBI426, and pCB13, were used in biolistic transformation. pBI434 modified pBI434 were used in *Agrobacterium*-mediated transformation The Ara h2 promoter is shown in FIG. 9.

PCB13 is used in co-bombardments with modified pBI426 which contains peanut allergen fragments (Ara h transgenes), to select transgenic plants. pCB13 contains the 35S promoter, hygromycin gene, and the nos terminator. This cassette is cloned into pUC19.

The plasmid pBI426 (Dalta et al., 1991 Gene 101: 239-246) contains a fusion gene (GUS fused to nptII) cloned between XbaI and SacI, and driven by the 35S promoter. Its also contains a nontranslatable leader sequence of 50 base pairs from Alfalfa Mosaic Virus. The entire expression cassette is cloned into pUC18.

In the modified pBI426 plasmid, for peanut transformation the gus-nptII fusion gene is replaced with DNA sequences from peanut allergens either as PCR products, or synthetic oligonucleotides. Ara h transgenes are clones as XbaI/SacI fragments in sense and antisense orientations. For comparative studies, 35S promoter is replaced with Arah2 promoter (shown in FIG. 9).

For *Agrobacterium*-mediated transformation of peanut, plasmid constructs pBI434 and modified pBI434 were used.

pBI434 is a binary vector derived from pBIN19. The T-DNA between the right border (RB) and the left border (LB) contains the 35S promoter, the 50 base pairs leader sequence from alfalfa mosaic virus, the fusion gene gus-nptII, and the nos terminator.

In the modified pBI434, the GUS gene is replaced by allergen DNA sequences (Ara h transgene) as XbaI/PstI fragments in sense and antisense orientations. NptII is the selection marker, and transgenic tissues are selected with kanamycin or paromomycin.

Example 3

Methodology Used in Peanut Tissue Culture, Transformation and Regeneration

Peanut Varieties

The most widely cultivated peanut cultivars in the USA, 'Florunner', 'New Mexico Valencia', 'Georgia Green', and 'Georgia Red' can be used in the present method, although a person skilled in the art will realize that the method is applicable to other peanut varieties.

Genetic Constructs

Efficient strategies to down-regulate genes in transgenic plants utilize antisense RNA, co-suppression, or double-stranded RNA. All three methods are being used to down-regulate peanut allergens. Transformation vectors used are pUC18 for biolistic transformation, and modified versions of pBI434 (Dalta et al, 1991), a binary vector for transformation using *Agrobacterium tumefaciens*. Transformation vectors carry the transgenes, flanked by a (the Arah2 promoter, shown in FIG. 9, or the 35S promoter) and the nopaline synthase terminator. Transgenes are portions of the open reading frame (ORF) of peanut allergens Arah1, Arah2, Arah3, Arah4, Arah5, Arah6, Arah7 genes, and any other peanut allergen genes. Previous studies show homologies between nucleotide sequences of the genomic DNA of Arah2, and Arah6 and Arah7 cDNAs (Viquez et al, 2000, see FIG. 3). Also, comparison between Arah3 and Arah4 cDNA sequences obtained from the gene bank, shows 95% homology. Different types of transformation cassettes are made to down-regulate peanut allergens.

Transformation cassettes type 1 are used to down-regulate Arah2, Arah6 and Arah7 in transgenic peanut. The homology region between nucleotide sequences of the above three allergen genes (FIG. 3), is PCR amplified from the genomic DNA of Arah2. The PCR product is then cloned into the transformation vectors (pBI426 or pBI434) in the antisense orientation for the antisense RNA strategy, or in sense orientation for the co-suppression strategy. The PCR product is also operably linked in frame as an antisense and sense fragment for the dsRNA strategy. Also, the antisense construct and sense construct are used in co-transformation for the dsRNA strategy.

Another alternative is to synthesize at least 100 base pairs oligonucleotides corresponding to the homology region, to be used as for the PCR products.

FIG. 3 shows the nucleotide sequences of the coding region of Arah2 genomic DNA (Viquez et al, 2000). The homology region between Arah2, Arah6 and Arah7 is shown in capital letters. This region is amplified by PCR and cloned into the transformation vectors (pUC18, or pBI434). Amplified region to be used for down-regulation of Arah2, Arah6, Ara h7 allergens is shown in capital letters. Alternative methods can be used such as 1) to synthesize at least 100 base pairs oligonucleotides within the region of homology, 2) to synthesize at least 100 base pairs oligonucleotides at the 5' end of the cDNA of each allergen gene. These oligonucleotides are used in the same way as for the PCR products.

Transformation Cassettes Type 2

Transformation cassettes type 2 are used to down-regulate Ara h3, and Ara h4 allergens in peanut. The cDNAs of these two allergens have 95% homology (FIG. 4). A portion of two hundred base pairs within the homology region is PCR amplified, and then cloned into the above transformation vectors in sense, and/or antisense orientation.

FIG. 4 shows the cDNA sequence of Arah h3 (Kleber-Janke, T, 1999). The amplified region to be used for downregulation of both Ara h3 and Ara h4 allergens is shown in capital letters. Alternative methods that may be used are 1) to synthesize at least 100 base pairs oligonucleotides within the region of homology, 2) to synthesize at least 100 base pairs oligonucleotides at the 5' end of the cDNA of each allergen gene. These oligonucleotides are used in the same way as for the PCR products.

Transformation Vectors Type 3

Transformation vectors type 3 are used to down-regulate the two clones of Ara h1 (Ara h 1 P41B, and Ara h 1 P17) in peanut. The cDNA sequence of these two clones show 96% homology. A portion of at least two hundred base pairs within the homology region is PCR amplified, and then cloned into the above transformation vectors in sense, and/or antisense orientation. FIG. 4 shows the nucleotide sequence of Ara h3 41B (Burk et al, 1995). The amplified region to be used for down-regulation of the two clones of Ara h1 allergens is shown in capital letters. Alternative methods that may be used are 1) to synthesize at least 100 base pairs oligonucleotides within the region of homology, 2) to synthesize at least 100 base pairs oligonucleotides at the 5' end of the cDNA of each allergen gene. These oligonucleotides are used in the same way as for the PCR products.

FIG. 5. shows the sequence of Ara h5 cDNA. This sequence does not have any homology with other allergens. The PCR amplified region for antisense and/or sense constructs are shown in bold to down-regulate Ara h1 proteins in peanut plants.

Promoters

Promoters are the key elements for gene expression. Peanut allergens are seed storage proteins. Therefore, to target the synthesis of peanut allergens, a seed specific promoter is essential. The inventive approach has developed its own promoter, the Arah 2 promoter, shown in FIG. 9 (see also Visqez et al, 2000; which is used to drive RNA transcripts of transgenes cloned into pBI426 and pBI434. In addition, for comparative studies, the Arah 2 promoter shown in FIG. 9 is replaced by the 35S promoter from Cauliflower Mosaic Virus, to compare the degree of downregulation. Whichever of the two types of promoter is used, the promoter is inserted into an expression cassette between HindIII and BglII sites, upstream of and the Ara h transgene PCR amplification product which is inserted between a nontranslatable leader sequence of 50 basepairs from Alfala Mosaic Virus, and a nos terminator.

Selection Marker

Plasmid pCB13 lox (see FIG. 8) is provided by Ozias-Akin (University of Georgia). This plasmid contains the hygromycin gene, driven by the 35S promoter. This plasmid is used to select transgenic peanut plants. In the case of transformation using *Agrobacterium tumefaciens*, plasmid pBI434 (Dalta et al., 1991; see FIG. 8) contains the neomycin phosphotransferase II gene for selection with paromomycin or kanamycin.

Reporter Gene

In some experiments, plasmid pBI426 carrying the GUS gene, driven by the 35S promoter, is used in co-bombardment with allergen construct, to monitor transformation in peanut.

Embryogenic cells of peanut variety Georgia green are co-bombarded with pBI426 (containing the gus gene), and pD2, a modified version of pBI426 plasmid which contains the sense construct of Ara h2, replacing the fusion gus-nptII gene. Transient GUS assays show transformation events as dark blue spots. Cultures are in selection medium. Embryos were excised from seeds of peanut cultivars “Florunner” and “Georgia green”.

All three types of transformation vectors described above are used in each of the strategies of the present invention for antisense transformation (using antisense constructs), co-suppression (using sense constructs), and the combining of antisense and sense constructs to generate in one transformation vector double stranded RNA fusion transcripts under the control of a single promoter (using either the Ara h2 promoter, or the 35S promoter), Constructs for fusion transcripts are used for both biolistic and *agrobacterium*-mediated transformation.

Peanut Regeneration from Somatic Embryos

Embryos are excised from seeds of peanut, and are sterilized for 30 min in 20% chlorox (v/v) on a shaker at 130 rpm. Seeds are rinsed four times in sterile distilled water, and embryo axes are then separated from cotyledons. Embryo axes are plated on MS medium (MS salts and nutrients (Sigma chemical co, St. Louis) supplemented with picloram (3 mg/l), glutamine (1 mg/l), sucrose (20 g/l). pH5.8, before autoclaving. Embryos are cultured, and maintained in dark. After about 3 weeks, proembry masses are formed on explants. They are subcultured every three weeks on the same medium.

Transformation

Embryo cultures are bombarded using a PDS1000/helium driven apparentus (Bio-rad Laboratories, Herculus, Calif.). Five μg is of DNA of each construct (single transformations), or five μg of total DNA (co-transformations) are used for biolistic transformation. Gold particles mixed with the transformation plasmids are accelerated using 1100 PSI pressure under a vacuum of 71 cm mercury. One bombardment is conducted for each transformation experiment. After bombardment, embryos are kept on the same medium for 3 days in dark. They are then transferred in liquid medium supplemented with 20 mg/l hygromycin for selection. The liquid medium is refreshed every two weeks. Cultures are maintained in dark with shaking at 130 rpm.

Regeneration

Transgenic structures are multiplied on MS+10 mg/l hygromycin+1 mg/l glutamin and maintained in dark for 2-3 weeks. Cultures are then transferred in light on MS+3 mg/l BAP+1 mg/l GA3 till embryos geminate. Germinated embryos are then transferred on rooting medium (MS+0.2 m/1 NAA). Hygromycin is also added to confirm transgenics, because non-transgenic plants will not grow.

Peanut Regeneration from Epicotyls

Sterile embryo axes are cultured on MSTDZ medium (MS medium supplemented with myo-inositol (100 mg/l), sucrose (30 g/l), and thidiazuron (2.2 ml of a 1 mg/ml stock). Culture media are adjusted to pH5.8, before autoclaving. Epicotyls are excised from 6 day old germinated embryos by an oblique cut below the cotyledon region, followed by a blunt cut above the root axis.

Transformation

Epicotyl sections are washed in ½ MSI solution (MS salts and nutrients (Sigma chemical co, St. Louis) (2.15 g/l and myo-inositol 1 g/l, pH5.8 sequentially for three times at 20 min each. Explants are then immersed in a solution of *Agrobacterium* diluted with MSI at OD600=0.5-1. Agro/explant mixture is swirled for ten min. Explants are then blotted on sterile towel paper, and then transferred on MSO (MS medium supplemented with myo-inositol (100 mg/l), sucrose (30 g/l) for five days co-culture. After the co-culture period, epicotyl explants are transferred on MSTDZ medium supplemented with 400 mg/l carbenicillin, and 200 mg/l kanamycin (selection) until shoot formation. Putative transgenic shoots are excised for transfer on rooting medium MSTDZ+50 mg/l kanamycin.

Example 4

Regeneration of Transformed Peanut and Verification of Antisense Expression and Level of Down Regulation of Peanut Allergens Transformed epicotyl sections are transferred to MSTDZ media supplemented with 200 mg of kanamycin per liter for selection. All plasmid vectors utilized contain kanamycin resistance genes. Epicotyl explants remain on this media for 2-3 weeks under 16 h/8 h light/dark and 26° C. incubation. Plasmid pBI434 contains the kanamycin resistance gene.

Regenerated shoots are excised and placed on MSO supplemented with 200 mg kanamycin per liter for selection. This step is for the detoxification of thidiazuron since this chemical prohibits root formation. Regenerated plants are grown on this media for 2-4 weeks under 16 h/8 h light/dark and 26° C. incubation.

Putative transgenic shoots are moved to rooting media (MSO supplemented with 50 mg of kanamycin per liter) for selection. Regenerated plants will remain on this media for 2-4 weeks under 16 h/8 h light/dark and 26° C. incubation.

When roots are sufficiently developed (2-5 roots, 2 cm or more in length), plantlets are moved to ⅓ Half Hogland solution (Sigma Chemical Co., St. Louis, Mo.) for 2-3 weeks to harden them prior to moving into soil.

Transient β-Glucuronidase (GUS) expression is determined 5 days after transformation. The intact explants or regenerated shoots are subjected to GUS histochemical assay (Jefferson et al., 1987, *EMBO J.* 16:2901-2907). Transformation events are dark blue spots.

Radiolabeling of the cDNA or partial genomic clones for Ara h1 and Ara h2 is performed using random oligonucleotides labeling (Amersham, Arlington Heights, Ill.) with $^{32}$P-dCTP. The labeled probes are used for the detection of stable integration of Ara h transgenes into transgenic plants.

Non-transformed controls is analyzed to determine basal levels of each gene in transgenic peanuts. The differences in allergen level of expression between the controls and the transformed peanut plants help in determining the level of downregulation in the transformed plants.

Copy number of transformants is also determined using Southern analysis as described in (Sambrook et al., supra). Great variability in the level of gene expression between individual transgenic plant containing the same introduced gene has been reported Rosahl et al., 1987. *EMBO J.* 6:1155-1159. This variability has been ascribed to various factors including gene copy number. A high correlation has been observed between gene copy number and increased gene expression.

An equal amount of digested (XbaI/SacI) and undigested (intact) genomic DNA (10 μg per lane) is separated by agarose gel electrophoresis using a 0.8% agarose gel, blotted onto a Hybond N$^+$ membrane (NEN Life Sciences, Boston Mass.). Hybridization probes were the synthetic 78 nucleotides DNA fragment for Ara h1 and the 80 nucleotides DNA fragment for Ara h2. Prehybridization, and hybridization is held at 60° C. for 2 hours and overnight, respectively. The membrane is washed twice for five minutes with 2×SSC (1×SSC is 0.15 M NaCl plus 0.15 M sodium citrate), 0.1% sodium dodecyl sulfate (SDS) and twice with 0.2×SSC, 0.2% SDS at 60° C. for 15 min. Detection of hybridization patterns is performed by autoradiography. The hybridization pattern is used to determine the copy number of the allergen genes per genome.

Enzyme-linked-immuno-sorbant-assay (ELISA) is performed to detect allergen levels in transgenic peanut plants. Proteins are extracted in a neutral pH phosphate buffer and ELISA conducted as described by Ausubel et al., 1995. In: *Short Protocols in Molecular Biology*. There are currently two commercial Elisa kits on the market for the detection of peanut residues: Neogen Corp. (Lansing, Mich.) and Elisa Technologies (Aluchua, Flor.)

Stable transformed peanut plants having undetectable or reduced or undetectable levels of peanut allergens are selected. Due to the use of Biolistics in the transformation of peanut, multiple copies of each gene are found in multiple locations of the genome, resulting in enhanced down-regulation.

Example 5

Verification of Transgene Transcripts, and Level of Down-Regulation of Peanut Allergens Radio-labeled probes, with 32P-dCTP of DNA sequences corresponding to the transgenes cloned into the transformation vectors, are used in southern and northern blots to detect stable transformations, copy number of transgenes, and RNA transcripts.

An equal amount of digested (XbaI/SacI) and undigested (intact) genomic DNA (10 μg per line) is separated by agarose gel electrophoresis using a 1% agarose gel, blotted onto a Hybond N$^+$ membrane (NEN Life Sciences, Boston Mass.). Prehybridization, and hybridization are held at 60° C. for 2 hours and overnight, respectively. The membrane is washed twice for five min with 2×SSC (1×SSC is 0.15 M NaCl plus 0.15M sodium citrate), 0.1% sodium dodecyl sulfate (SDS), and twice with 0.2×SSC, 0.2% SDS at 60° C. for 15 min. Detection of hybridization patterns is performed by autoradiography.

Enzyme-linked-immuno-sorbant-assay (ELISA) is performed to detect allergen levels in transgenic peanut plants. Proteins are extracted in a neutral pH phosphate buffer and ELISA conducted as described by Ausubel et al., 1995. In: *Short Protocols in Molecular Biology*. There are currently two commercial ELISA kits on the market for the detection of peanut residues: Neogen Corp. (Lansing, Mich.) and ELISA Technology (Aluchua, Flor.) Stable transformed peanut plants having undetectable or reduced levels of allergens are selected.

We claim:

1. A regenerated fertile transgenic peanut plant that is the product of the process comprising:

(a) cloning a homologous region common to more than one gene selected from the group consisting of Ara h1, Ara h2, Ara h3, Ara h4, Ara h6, and Ara h7 wherein said more than one gene codes for more than one allergen protein, or the antisense sequence of the homologous region in a vector for peanut transformation, wherein the homologous region or its antisense sequence is operably linked to a promoter; and (b) transforming a recipient peanut plant cell with the vector to generate a transgenic peanut plant, wherein said plant produces seed having reduced or undetectable levels of at least one of the said more than one allergen protein content compared to wild-type.

2. The plant of claim 1, comprising the homologous region and the antisense sequence of the homologous region operably linked to a promoter.

3. The plant of claim 1, wherein the homologous region is selected from the group consisting of: SEQ ID NO: 2, SEQ ID NO: 10, SEQ ID NO: 11, and a fragment of any of the foregoing.

4. The plant of claim 1, wherein the promoter is a seed preferred promoter.

5. The plant of claim 1, wherein a seed of the plant displays reduced or eliminated expression of said more than one allergen protein compared to wild-type.

6. The plant of claim 1, wherein the plant displays reduced or eliminated expression of each of the more than one allergen proteins to which the homologous region is common compared to wild-type.

7. A transgenic seed of the plant of claim 1 having reduced or undetectable levels of at least one of the said more than one allergen protein content compared to wild-type.

8. An *Arachis hypogaea* cell comprising a gene operably linked to a promoter, the gene comprising an antisense sequence selected from the group consisting of: the antisense sequence of SEQ ID NO: 3, the antisense sequence of SEQ ID NO: 4, the antisense sequence of SEQ ID NO: 5, the antisense sequence of SEQ ID NO: 6, and a fragment of any of the forgoing; wherein the cell has reduced or undetectable levels of at least one allergen protein selected from the group consisting of Ara h1, h2, h3, h4, h5, h6, and h7 compared to wild-type when the gene is expressed.

9. The cell of claim 8, wherein the gene comprises the antisense sequence of a region common to more than one Ara h allergen gene, the region selected from the group consisting of: SEQ ID NO: 9, SEQ ID NO: 10, SEQ ID NO: 11, and a fragment of any of the foregoing.

10. The cell of claim 8, wherein the gene comprises an antisense sequence selected from the group consisting of: the antisense sequence of SEQ ID NO: 3, the antisense sequence of SEQ ID NO: 4, and the antisense sequence of SEQ ID NO: 5.

11. The cell of claim 8, wherein the promoter is a seed-preferred promoter.

12. The cell of claim 8 further comprising the antisense sequence of the gene operably linked to a second promoter.

13. The cell of claim 12, wherein the second promoter is a seed-preferred promoter.

14. The cell of claim 12, wherein the first promoter and second promoter are the same.

15. The cell of claim 9, wherein the cell displays reduced or eliminated expression of each of the more than one Ara h allergens to which the region is common compared to wild-type.

16. A transgenic plant comprising the cell of claim 8.

17. A transgenic seed of the plant of claim 16 wherein the seed has reduced or undetectable levels of at least one allergen protein selected from the group consisting of Ara h1, h2, h3, h4, h5, h6, and h7 compared to wild-type.

18. A peanut seed comprising the cell of claim 8.

19. The regenerated fertile transgenic peanut plant of claim 1 further comprising an antisense sequence selected from the group consisting of: the antisense sequence of SEQ ID NO: 16; and the antisense sequence of a fragment of SEQ ID NO: 16.

20. The cell of claim 8 further comprising an antisense sequence selected from the group consisting of: the antisense sequence of SEQ ID NO: 16; and the antisense sequence of a fragment of SEQ ID NO: 16.

21. An *Arachis hypogaea* cell comprising a heterologous gene operably linked to a promoter, the gene comprising an antisense sequence selected from the group consisting of: the antisense sequence of SEQ ID NO: 9, the antisense sequence of SEQ ID NO: 10, the antisense sequence of SEQ ID NO: 11, and the antisense sequence of SEQ ID NO: 6.

22. The cell of claim 21, wherein the gene comprises an antisense sequence selected from the group consisting of: the antisense sequence of SEQ ID NO: 3, the antisense sequence of SEQ ID NO: 4, and the antisense sequence of SEQ ID NO: 5.

23. The cell of claim 21, wherein the promoter is a seed-preferred promoter.

24. The cell of claim 21 further comprising a second gene, the second gene comprising an antisense sequence selected from the group consisting of: the antisense sequence of SEQ ID NO: 3, the antisense sequence of SEQ ID NO: 4, the antisense sequence of SEQ ID NO: 5, the antisense sequence of SEQ ID NO: 6, and a fragment of any of the forgoing; the second gene operably linked to a second promoter.

25. The cell of claim 24, wherein the second promoter is a seed-preferred promoter.

26. The cell of claim 24, wherein the first promoter and second promoter are the same.

27. The cell of claim 21, wherein the cell displays reduced or eliminated expression of each of the more than one Ara h allergens to which the region is common compared to wild-type.

28. A transgenic plant comprising the cell of claim 21.

29. A seed of the plant of claim 28 wherein the seed has reduced or undetectable levels of at least one allergen protein selected from the group consisting of Ara h1, h2, h3, h4, h5, h6, and h7 compared to wild-type.

30. A peanut seed comprising the cell of claim 21.

* * * * *

SEQUENCE LISTING

```
<160> NUMBER OF SEQ ID NOS: 18

<210> SEQ ID NO 1
<211> LENGTH: 1162
<212> TYPE: DNA
<213> ORGANISM: Arachis hypogaea
```

-continued

<400> SEQUENCE: 1

```
tccttacgcg aaatacgggc agacatggcc tgcccggtta ttattatttt tgacacagac     60
caactggtaa tggtagcgac cggcgctcag ctggaattcg cggccgccaa tggccaagct    120
caccatacta gtagccctcg cccttttcct cctcgctgcc cacgcatctg cgaggcagca    180
gtgggaactc caaggagaca gaagatgcca gagccagctc gagagggcga acctgaggcc    240
ctgcgagcaa catctcatgc agaagatcca acgtgacgag gattcatatg aacgggaccc    300
gtacagccct agtcaggatc cgtacagccc tagtccatat gatcggagag gcgctggatc    360
ctctcagcac caagagaggt gttgcaatga gctgaacgag tttgagaaca accaaaggtg    420
catgtgcgag gcattgcaac agatcatgga gaaccagagc gataggttgc aggggaggca    480
acaggagcaa cagttcaaga gggagctcag gaacttgcct caacagtgcg gccttagggc    540
accacagcgt tgcgacttgg acgtcgaaag tggcggcagg cggccgcgaa ttccgccgat    600
actgacgggc tccaggagtc gtcgccacca atccccatat ggaaaccgtc gatattcagc    660
catgtgcctt cttccgcgtg cagcagatgg cgatggctgg tttccatcag ttgctgttga    720
ctgtagcggc tgatgttgaa ctggaagtcg ccgcgccact ggtgtgggcc ataattcaat    780
tcgcgcgtcc cgcagcgcag accgttttcg ctcgggaaga cgtacggggt atacatgtct    840
gacaatggca gatcccagcg gtcaaaacag gcggcagtaa ggcggtcggg atagttttct    900
tgcggcccta atccgagcca gtttacccgc tctgctacct gcgccagctg gcagttcaag    960
ccaatccgcg ccggatgcgg tgtatcgctc gccacttcaa catcaacggt aatcgccatt   1020
tgaccactac catcaatccg gtaggttttc cggctgataa ataaaggttt tcccctgatg   1080
ctgccacgcg tgagcggtcg taatcagcac cgcatcaaca agtgtatttt gccgtgcact   1140
gcaacaacgc tggttcgggc tg                                            1162
```

<210> SEQ ID NO 2
<211> LENGTH: 207
<212> TYPE: PRT
<213> ORGANISM: Arachis hypogaea

<400> SEQUENCE: 2

```
Met Ala Lys Leu Thr Ile Leu Val Ala Leu Ala Leu Phe Leu Leu Ala
1               5                   10                  15

Ala His Ala Ser Ala Arg Gln Gln Trp Glu Leu Gln Gly Asp Arg Arg
            20                  25                  30

Cys Gln Ser Gln Leu Glu Arg Ala Asn Leu Arg Pro Cys Glu Gln His
        35                  40                  45

Leu Met Gln Lys Ile Gln Arg Asp Glu Asp Ser Tyr Glu Arg Asp Pro
    50                  55                  60

Tyr Ser Pro Ser Gln Asp Pro Tyr Ser Pro Ser Pro Tyr Asp Arg Arg
65                  70                  75                  80

Gly Ala Gly Ser Ser Gln His Gln Glu Arg Cys Cys Asn Glu Leu Asn
                85                  90                  95

Glu Phe Glu Asn Asn Gln Arg Cys Met Cys Glu Ala Leu Gln Gln Ile
            100                 105                 110

Met Glu Asn Gln Ser Asp Arg Leu Gln Gly Arg Gln Gln Glu Gln Gln
        115                 120                 125

Phe Lys Arg Glu Leu Arg Asn Leu Pro Gln Gln Cys Gly Leu Arg Ala
    130                 135                 140

Pro Gln Arg Cys Asp Leu Asp Val Glu Ser Gly Gly Arg Arg Pro Arg
145                 150                 155                 160
```

-continued

```
Ile Pro Pro Ile Leu Thr Gly Ser Arg Ser Arg Arg His Gln Ser Pro
                165                 170                 175

Tyr Gly Asn Arg Arg Tyr Ser Ala Met Cys Leu Leu Pro Arg Ala Ala
            180                 185                 190

Asp Gly Asp Gly Trp Phe Pro Ser Val Ala Val Asp Cys Ser Gly
        195                 200                 205


<210> SEQ ID NO 3
<211> LENGTH: 682
<212> TYPE: DNA
<213> ORGANISM: Arachis hypogaea

<400> SEQUENCE: 3

gacacagacc aactggtaat ggtagcgacc ggcgctcagc tggaattcgc ggccgccaat      60

ggccaagctc accatactag tagccctcgc ccttttcctc ctcgctgccc acgcatctgc     120

gaggcagcag tgggaactcc aaggagacag aagatgccag agccagctcg agagggcgaa     180

cctgaggccc tgcgagcaac atctcatgca gaagatccaa cgtgacgagg attcatatga     240

acgggacccg tacagcccta gtcaggatcc gtacagccct agtccatatg atcggagagg     300

cgctggatcc tctcagcacc aagagaggtg ttgcaatgag ctgaacgagt ttgagaacaa     360

ccaaaggtgc atgtgcgagg cattgcaaca gatcatggag aaccagagcg ataggttgca     420

ggggaggcaa caggagcaac agttcaagag ggagctcagg aacttgcctc aacagtgcgg     480

ccttagggca ccacagcgtt gcgacttgga cgtcgaaagt ggcggcaggc ggccgcgaat     540

tccgccgata ctgacgggct ccaggagtcg tcgccaccaa tccccatatg gaaaccgtcg     600

atattcagcc atgtgccttc ttccgcgtgc agcagatggc gatggctggt ttccatcagt     660

tgctgttgac tgtagcggct ga                                              682


<210> SEQ ID NO 4
<211> LENGTH: 1853
<212> TYPE: DNA
<213> ORGANISM: Arachis hypogaea

<400> SEQUENCE: 4

atggctaagc ttcttgagct ttctttttgc ttttgctttc tagttctggg agctagcagc      60

atctccttca ggcagcagcc ggaggagaat gcgtgccagt tccagcgcct caatgcgcag     120

agacctgaca accgcattga atcggagggc ggttacattg agacttggaa ccccaacaac     180

caggagttcg aatgcgccgg cgtcgccctc tctcgcttag tcctccgccg caacgccctt     240

cgtaggcctt tctactccaa tgctccccag gagatcttca tccagcaagg aaggggatac     300

tttgggttga tattccctgg ttgtcctagc acatatgaag agcctgcaca acaaggacgc     360

cgatatcagt cccaaagacc accaagacgt ttgcaagaag aagaccaaag ccaacagcaa     420

caagatagtc accagaaggt gcaccgtttc aatgagggtg atctcattgc agttcccacc     480

ggtgttgctt tctggctgta caacgaccac gacactgatg ttgttgctgt ttctcttact     540

gacaccaaca acaacgacaa ccagcttgat cagttcccca ggagattcaa tttggctggg     600

aaccacgagc aagagttctt aaggtaccag caacaaagca gacaaagcag acgaagaagc     660

ttaccatata gcccatacag cccgcatagt cggcctagac gagaagagcg tgaatttcgc     720

cctcgaggac agcacagccg cagagaacga gcaggacaag aagaagaaga cgaaggtgga     780

aacatcttca gcggcttcac gccggagttc ctggaacaag ccttccaggt tgacgacaga     840

cagattgtgc aaaatctgtg gggcgagaac gagagtgaag aagagggagc cattgtgacg     900

gtgaggggag gcctcagaat cttgagccca gatggaacga gaggtgccga cgaagaagag     960
```

-continued gaatacgatg aagatcaata tgaataccat gaacaggatg gaaggcgtgg caggggaagc 1020
agaggcgggg ggaatggtat tgaagagacg atctgcaccg catgtgttaa aaagaacatt 1080
ggtggaaaca gatcccctca catctacgat cctcagcgct ggttcactca aaactgccac 1140
gatctcaacc ttctaatcct taggtggctt ggacttagtg ctgaatatgg aaatctctac 1200
aggaatgcat tgtttgtccc tcactacaac accaacgcac acagcatcat atatgcattg 1260
aggggacggg ctcacgtgca agtggtggac agcaacggca acagagtgta cgacgaggag 1320
cttcaagagg gtcacgttct tgtggtgcca cagaacttcg ccgtggctgg gaagtcccag 1380
agcgagaact tcgaatacgt ggcattcaag acagattcaa ggcccagcat agccaacttt 1440
gccggtgaaa actccttcat agataacctg ccggaggagg tggttgcaaa ttcatatggc 1500
ctcccaaggg agcaggcaag gcagcttaag aacaacaacc ccttcaagtt cttcgttcca 1560
ccttttcagc agtctccgag ggctgtggct taaaaacgac cagtatcttt tgcaagcgtg 1620
ttatccacta acataacttt ttgccacaaa tgaataatat aataataaga agaataatgt 1680
agttttaatt tttagtatga ataagaatac aaaggggcat tgatgccttt ttgtttaaga 1740
tcggaatgta acatatgtgc aatgagcaga tatggagaaa accttttgcg ggaaaaacat 1800
gaataataaa agaagttatg gtctcacgca aaaaaaaaaa aaaaaaaaaa aaa 1853

<210> SEQ ID NO 5
<211> LENGTH: 2032
<212> TYPE: DNA
<213> ORGANISM: Arachis hypogaea

<400> SEQUENCE: 5
aataatcata tatattcatc aatcatctat ataagtagta gcaggagcaa tgagagggag 60
ggtttctcca ctgatgctgt tgctagggat ccttgtcctg gcttcagttt ctgcaacgca 120
tgccaagtca tcaccttacc agaagaaaac agagaacccc tgcgcccaga ggtgcctcca 180
gagttgtcaa caggaaccgg atgacttgaa gcaaaaggca tgcgagtctc gctgcaccaa 240
gctcgagtat gatcctcgtt gtgtctatga tcctcgagga cacactggca ccaccaacca 300
acgttcccct ccaggggagc ggacacgtgg ccgccaaccc ggagactacg atgatgaccg 360
ccgtcaaccc cgaagagagg aaggaggccg atggggacca gctggaccga gggagcgtga 420
aagagaagaa gactggagac aaccaagaga agattggagg cgaccaagtc atcagcagcc 480
acggaaaata aggcccgaag gaagagaagg agaacaagag tggggaacac caggtagcca 540
tgtgagggaa gaaacatctc ggaacaaccc tttctacttc ccgtcaaggc ggtttagcac 600
ccgctacggg aaccaaaacg gtaggatccg ggtcctgcag aggtttgacc aaaggtcaag 660
gcagtttcag aatctccaga atcaccgtat tgtgcagatc gaggccaaac ctaacactct 720
tgttcttccc aagcacgctg atgctgataa catccttgtt atccagcaag ggcaagccac 780
cgtgaccgta gcaaatggca ataacagaaa gagctttaat cttgacgagg gccatgcact 840
cagaatccca tccggtttca tttcctacat cttgaaccgc catgacaacc agaacctcag 900
agtagctaaa atctccatgc ccgttaacac acccggccag tttgaggatt tcttcccggc 960
gagcagccga gaccaatcat cctacttgca gggcttcagc aggaatacgt tggaggccgc 1020
cttcaatgcg gaattcaatg agatacggag ggtgctgtta gaagagaatg caggaggtga 1080
gcaagaggag agagggcaga ggcgatggag tactcggagt agtgagaaca atgaaggagt 1140
gatagtcaaa gtgtcaaagg agcacgttga agaacttact aagcacgcta aatccgtctc 1200
aaagaaaggc tccgaagaag agggagatat caccaaccca atcaacttga gagaaggcga 1260

```
gcccgatctt tctaacaact ttgggaagtt atttgaggtg aagccagaca agaagaaccc   1320

ccagcttcag gacctggaca tgatgctcac ctgtgtagag atcaaagaag gagctttgat   1380

gctcccacac ttcaactcaa aggccatggt tatcgtcgtc gtcaacaaag gaactggaaa   1440

ccttgaactc gtggctgtaa gaaaagagca acaacagagg ggacggcggg aagaagagga   1500

ggacgaagac gaagaagagg agggaagtaa cagagaggtg cgtaggtaca cagcgaggtt   1560

gaaggaaggc gatgtgttca tcatgccagc agctcatcca gtagccatca acgcttcctc   1620

cgaactccat ctgcttggct tcggtatcaa cgctgaaaac aaccacagaa tcttccttgc   1680

aggtgataag gacaatgtga tagaccagat agagaagcaa gcgaaggatt tagcattccc   1740

tgggtcgggt gaacaagttg agaagctcat caaaaaccag aaggaatctc actttgtgag   1800

tgctcgtcct caatctcaat ctcaatctcc gtcgtctcct gagaaagagt ctcctgagaa   1860

agaggatcaa gaggaggaaa accaaggagg gaagggtcca ctcctttcaa ttttgaaggc   1920

ttttaactga gaatggaggc aacttgttat gtatcgataa taagatcacg cttttgtact   1980

ctactatcca aaaacttatc aataaataaa aacgtttgtg cgttgtttct cc           2032
```

<210> SEQ ID NO 6
<211> LENGTH: 743
<212> TYPE: DNA
<213> ORGANISM: Arachis hypogaea

<400> SEQUENCE: 6

```
agaaagagaa gacaagatgt cgtggcaaac ctacgtcgat aaccaccttc tctgcgaaat     60

tgaaggcgac cacctctcct ccgccgcaat cctcggccaa gacggcggtg tttgggctca    120

gagctctcat ttccctcagt tcaagcctga ggaaattact gctatcatga acgactttgc    180

tgagcctgga tcgctcgccc ctaccgggtt gtacctcggt ggcaccaaat acatggttat    240

ccaaggtgaa cccggagcta tcattccagg gaagaagggt cctggtggtg ttaccattga    300

gaagacgaat caggcgttaa tcatcggaat ctacgataag ccaatgactc cggggcagtg    360

caacatgatt gttgaaaggc tgggtgatta tctcattgat acgggtcttt aagtcctctt    420

tgttatttct tgttatctgc ttgcttattt cactggctcc tatacgaggc ttcgcatcga    480

tgtgccaaga gaatgctcga ttgtagtgta ataatattaa ttgatgggta ttcaaaagtc    540

atgggatctg cgtctaggga agaagttatg gtgcttgaga agtgaatgat aactatcatc    600

tctgttgttg tgctttttag cgggtatctg tatacaattt acaagtggtt ttaatgctgt    660

gggcataaat gggcattaaa aaaaaaaaaa aaaaaaaaaa aaaaaaaaaa aaaaaaaaaa    720

aaaaaaaaaa aaaaaaaaaa aaa                                            743
```

<210> SEQ ID NO 7
<211> LENGTH: 80
<212> TYPE: DNA
<213> ORGANISM: Artificial Sequence
<220> FEATURE:
<223> OTHER INFORMATION: Probe

<400> SEQUENCE: 7

```
ctagtagccc tcgccctttt cctcctcgct gcccacgcat ctgcgaggca gcagtgggaa     60

ctccaaggag acagaagatg                                                 80
```

<210> SEQ ID NO 8
<211> LENGTH: 62
<212> TYPE: DNA
<213> ORGANISM: ARTIFICIAL SEQUENCE

<220> FEATURE:
<223> OTHER INFORMATION: Probe

<400> SEQUENCE: 8
gtgcatgtgc gaggcattgc aacagatcat ggagaaccag agcgataggt tgcaggggag 60
gc 62

<210> SEQ ID NO 9
<211> LENGTH: 207
<212> TYPE: DNA
<213> ORGANISM: Arachis hypogaea

<400> SEQUENCE: 9
aagagaggtg ttgcaatgag ctgaacgagt ttgagaacaa ccaaaggtgc atgtgcgagg 60
cattgcaaca gatcatggag aaccagagcg ataggttgca ggggaggcaa caggagcaac 120
agttcaagag ggagctcagg aacttgcctc aacagtgcgg ccttagggca ccacagcgtt 180
gcgacttgga cgtcgaaagt ggcggca 207

<210> SEQ ID NO 10
<211> LENGTH: 751
<212> TYPE: DNA
<213> ORGANISM: Arachis hypogaea
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (63)..(70)
<223> OTHER INFORMATION: n is a, c, g, or t
<220> FEATURE:
<221> NAME/KEY: misc_feature
<222> LOCATION: (175)..(178)
<223> OTHER INFORMATION: n is a, c, g, or t
<220> FEATURE:
<221> NAME/KEY: misc_feature
<222> LOCATION: (258)..(259)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (471)..(472)
<223> OTHER INFORMATION: n is a, c, g, or t
<220> FEATURE:
<221> NAME/KEY: misc_feature -continued
<222> LOCATION: (505)..(515)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (635)..(637)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (679)..(682)
<223> OTHER INFORMATION: n is a, c, g, or t

<400> SEQUENCE: 10
caccagaagg ngcaccgttt cnatgagggt gatctcattg cagttcccac cggtgttgct 60
ttnnnnnnnn acaacgacca cgacactgat gttgttgctg tttctcttac tgacaccaac 120
aacaacgaca accagcttga tcagttcccc aggagattca atttggctgg gaacnnnnag 180
caagagttct taaggtacca gcaacaaagc agacaaagca gacgaagaag cttaccatat 240
agcccataca gcccgcanng tcngcctaga cnagaagagc gtgaatttng ccctcgagga 300
cagcacagcc gcagagaacg agcaggacaa gaagaagaan acgaaggtgg aaacatcttc 360
agcggcttca cgccggagtt cctggaacaa gccttccagg ttgacgacag acagattgtg 420
caaaanctgt ggggcgagan cgagagtgaa gaagagggag ccattgtgac nntgagggga 480
ggcctcagaa tcttgagccc agatnnnnnn nnnnntgccg acgaagaaga ggaatacgat 540
gaagatcaat atgaatacna tgaanaggat ngaaggcgtg gcaggggaag cagaggcggg 600
gggaatggta ttgaagagac gatctgcacc gcatnnntta aaaagaacat tggtngaaac 660
agatcccctn acatctacnn nnctcagcgc tggttcactc aaaactgcca cgatctcaac 720
cttctaatcc ttaggtggct tggacttagt g 751

<210> SEQ ID NO 11
<211> LENGTH: 254
<212> TYPE: DNA
<213> ORGANISM: Arachis hypogaea
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (202)..(205)
<223> OTHER INFORMATION: n is a, c, g, or t

<400> SEQUENCE: 11
ccagaatcac cgtattgtgc agatcgaggc canncctaac actcttgttc ttcccaagca 60

-continued cgctgatgct gataacatcc ttgttatcca gcaaggnnaa gccaccgtga ccgtagcaaa 120
tggcaataac agaaagagct ttaatcttga cgagggccat gcactcagaa tcccatccgg 180
tttcatttcc tacatcttga annnncatga caaccagaac ctcagagtag ctaaaatctc 240
catgcccgtt aaca 254

<210> SEQ ID NO 12
<211> LENGTH: 2032
<212> TYPE: DNA
<213> ORGANISM: Arachis hypogaea

<400> SEQUENCE: 12
aataatcata tatattcatc aatcatctat ataagtagta gcaggagcaa tgagagggag 60
ggtttctcca ctgatgctgt tgctagggat ccttgtcctg gcttcagttt ctgcaacgca 120
tgccaagtca tcaccttacc agaagaaaac agagaacccc tgcgcccaga ggtgcctcca 180
gagttgtcaa caggaaccgg atgacttgaa gcaaaaggca tgcgagtctc gctgcaccaa 240
gctcgagtat gatcctcgtt gtgtctatga tcctcgagga cacactggca ccaccaacca 300
acgttcccct ccaggggagc ggacacgtgg ccgccaaccc ggagactacg atgatgaccg 360
ccgtcaaccc cgaagagagg aaggaggccg atggggacca gctggaccga gggagcgtga 420
aagagaagaa gactggagac aaccaagaga agattggagg cgaccaagtc atcagcagcc 480
acggaaaata aggcccgaag gaagagaagg agaacaagag tggggaacac caggtagcca 540
tgtgagggaa gaaacatctc ggaacaaccc tttctacttc ccgtcaaggc ggtttagcac 600
ccgctacggg aaccaaaacg gtaggatccg ggtcctgcag aggtttgacc aaaggtcaag 660
gcagtttcag aatctccaga atcaccgtat tgtgcagatc gaggccaaac ctaacactct 720
tgttcttccc aagcacgctg atgctgataa catccttgtt atccagcaag ggcaagccac 780
cgtgaccgta gcaaatggca ataacagaaa gagctttaat cttgacgagg gccatgcact 840
cagaatccca tccggtttca tttcctacat cttgaaccgc catgacaacc agaacctcag 900
agtagctaaa atctccatgc ccgttaacac acccggccag tttgaggatt tcttcccggc 960
gagcagccga gaccaatcat cctacttgca gggcttcagc aggaatacgt tggaggccgc 1020
cttcaatgcg gaattcaatg agatacggag ggtgctgtta gaagagaatg caggaggtga 1080
gcaagaggag agagggcaga ggcgatggag tactcggagt agtgagaaca atgaaggagt 1140
gatagtcaaa gtgtcaaagg agcacgttga agaacttact aagcacgcta aatccgtctc 1200
aaagaaaggc tccgaagaag agggagatat caccaaccca atcaacttga gagaaggcga 1260
gcccgatctt tctaacaact ttgggaagtt atttgaggtg aagccagaca agaagaaccc 1320
ccagcttcag gacctggaca tgatgctcac ctgtgtagag atcaaagaag gagctttgat 1380
gctcccacac ttcaactcaa aggccatggt tatcgtcgtc gtcaacaaag gaactggaaa 1440
ccttgaactc gtggctgtaa gaaaagagca acaacagagg ggacggcggg aagaagagga 1500
ggacgaagac gaagaagagg agggaagtaa cagagaggtg cgtaggtaca cagcgaggtt 1560
gaaggaaggc gatgtgttca tcatgccagc agctcatcca gtagccatca acgcttcctc 1620
cgaactccat ctgcttggct tcggtatcaa cgctgaaaac aaccacagaa tcttccttgc 1680
aggtgataag gacaatgtga tagaccagat agagaagcaa gcgaaggatt tagcattccc 1740
tgggtcgggt gaacaagttg agaagctcat caaaaaccag aaggaatctc actttgtgag 1800
tgctcgtcct caatctcaat ctcaatctcc gtcgtctcct gagaaagagt ctcctgagaa 1860
agaggatcaa gaggaggaaa accaaggagg gaagggtcca ctcctttcaa ttttgaaggc 1920
ttttaactga gaatggaggc aacttgttat gtatcgataa taagatcacg cttttgtact 1980
ctactatcca aaaacttatc aataaataaa aacgtttgtg cgttgtttct cc 2032

<210> SEQ ID NO 13
<211> LENGTH: 1949
<212> TYPE: DNA
<213> ORGANISM: Arachis hypogaea

<400> SEQUENCE: 13
caatgagagg gagggtttct ccactgatgc tgttgcttgg gatccttgtc ctggcttcag 60
tttctgcaac gcaggccaag tcaccttacc ggaaaacaga gaacccctgc gcccagaggt 120
gcctccagag ttgtcaacag gaaccggacg acttgaagca aaaggcatgc gagtctcgct 180
gcaccaagct cgagtatgat cctcgttgtg tctatgacac tggcgccacc aaccaacgtc 240
accctccagg ggagcggaca cgtggccgcc aacccggaga ctacgatgat gaccgccgtc 300
aaccccgaag agaggaagga ggccgatggg gaccagctga accgagggag cgtgaaagag 360
aagaagactg gagacaacca agagaagatt ggaggcgacc aagtcatcag cagccacgga 420
aaataaggcc cgaaggaaga gaaggagaac aagagtgggg aacaccaggt agcgaggtga 480
gggaagaaac atcacggaac aaccctttct acttcccgtc aaggcggttt agcacccgct 540
acgggaacca aaacggtagg atccgcgtcc tgcagaggtt tgaccaaagg tcaaagcagt 600
ttcagaatct ccagaatcac cgtattgtgc agatcgaggc cagacctaac actcttgttc 660
ttcccaagca cgctgatgct gataacatcc ttgttatcca gcaaggacaa gccaccgtga 720
ccgtagcaaa tggcaataac agaaagagct ttaatcttga cgagggccat gcactcagaa 780
tcccatccgg tttcatttcc tacatcttga atcgacatga caaccagaac ctcagagtag 840
ctaaaatctc catgcccgtt aacacgcccg gccagtttga ggatttcttc ccggcgagca 900
gccgagacca atcatcctac ttgcagggat tcagcaggaa tactttggag gccgccttca 960
atgcggaatt caatgagata cggagggtgc tgttagaaga gaatgcagga ggagagcaag 1020
aggagagagg gcagaggcga cggagtactc ggagtagtga taatgaagga gtgatagtca 1080
aagtgtcaaa ggagcacgtt caagaactta ctaagcacgc taaatccgtc tcaaagaaag 1140
gctccgaaga ggaagatatc accaacccaa tcaacttgag agatggcgag cccgatcttt 1200
ctaacaactt tgggaggtta tttgaggtga agccagacaa gaagaacccc cagcttcagg 1260
acctggacat gatgctcacc tgtgtagaga tcaaagaagg agctttgatg ctcccacact 1320
tcaactcaaa ggccatggtc atcgtcgtcg tcaacaaagg aactggaaac cttgaactcg 1380
tagctgtaag aaaagagcaa caacagaggg gacggcggga acaagagtgg gaagaagagg 1440
aggaagatga agaagaggag ggaagtaaca gagaggtgcg taggtacaca gcgaggttga 1500
aggaaggcga tgtgttcatc atgccagcag ctcatccagt agccatcaac gcttcctccg 1560
aactccatct gcttggcttc ggtatcaacg ctgaaaacaa ccacagaatc ttccttgcag 1620
gtgataagga caatgtgata gaccagatag agaagcaagc gaaggattta gcattccctg 1680
gttcgggtga acaagttgag aagctcatca aaaaccagag ggagtctcac tttgtgagtg 1740
ctcgtcctca atctcaatct ccgtcgtctc ctgaaaaaga ggatcaagag gaggaaaacc 1800
aaggagggaa gggtccactc ctttcaattt tgaaggcttt taactgagaa tggaggaaac 1860
ttgttatgta tccataataa gatcacgctt ttgtaatcta ctatccaaaa acttatcaat 1920
aaataaaaac gtttgtgcgt tgtttctcc 1949

<210> SEQ ID NO 14
<211> LENGTH: 1524
<212> TYPE: DNA
<213> ORGANISM: Arachis hypogaea

<400> SEQUENCE: 14

```
cggcagcaac cggaggagaa cgcgtgccag ttccagcgcc tcaatgcgca gagacctgac     60
aatcgcattg aatcagaggg cggttacatt gagacttgga accccaacaa ccaggagttc    120
gaatgcgccg gcgtcgccct ctctcgctta gtcctccgcc gcaacgccct tcgtaggcct    180
ttctactcca atgctcccca ggagatcttc atccagcaag gaaggggata ctttgggttg    240
atattccctg gttgtcctag acactatgaa gagcctcaca cacaaggtcg tcgatctcag    300
tcccaaagac caccaagacg tctccaagga gaagaccaaa gccaacagca acgagatagt    360
caccagaagg tgcaccgttt cgatgagggt gatctcattg cagttcccac cggtgttgct    420
ttctggctct acaacgacca cgacactgat gttgttgctg tttctcttac tgacaccaac    480
aacaacgaca accagcttga tcagttcccc aggagattca atttggctgg gaacacggag    540
caagagttct taaggtacca gcaacaaagc agacaaagca gacgaagaag cttaccatat    600
agcccataca gcccgcaaag tcagcctaga caagaagagc gtgaatttag ccctcgagga    660
cagcacagcc gcagagaacg agcaggacaa gaagaagaaa acgaaggtgg aaacatcttc    720
agcggcttca cgccggagtt cctggaacaa gccttccagg ttgacgacag acagatagtg    780
caaaacctaa gaggcgagac cgagagtgaa gaagagggag ccattgtgac agtgagggga    840
ggcctcagaa tcttgagccc agatagaaag agacgtgccg acgaagaaga ggaatacgat    900
gaagatgaat atgaatacga tgaagaggat agaaggcgtg gcaggggaag cagaggcagg    960
gggaatggta ttgaagagac gatctgcacc gcaagtgcta aaaagaacat tggtagaaac   1020
agatcccctg acatctacaa ccctcaagct ggttcactca aaactgccaa cgatctcaac   1080
cttctaatac ttaggtggct tggacctagt gctgaatatg gaaatctcta caggaatgca   1140
ttgtttgtcg ctcactacaa caccaacgca cacagcatca tatatcgatt gaggggacgg   1200
gctcacgtgc aagtcgtgga cagcaacggc aacagagtgt acgacgagga gcttcaagag   1260
ggtcacgtgc ttgtggtgcc acagaacttc gccgtcgctg gaaagtccca gagcgagaac   1320
ttcgaatacg tggcattcaa gacagactca aggcccagca tagccaacct cgccggtgaa   1380
aactccgtca tagataacct gccggaggag gtggttgcaa attcatatgg cctccaaagg   1440
gagcaggcaa ggcagcttaa gaacaacaac cccttcaagt tcttcgttcc accgtctcag   1500
cagtctccga gggctgtggc ttaa                                          1524
```

<210> SEQ ID NO 15
<211> LENGTH: 1853
<212> TYPE: DNA
<213> ORGANISM: Arachis hypogaea

<400> SEQUENCE: 15

```
atggctaagc ttcttgagct ttcttttttgc ttttgctttc tagttctggg agctagcagc     60
atctccttca ggcagcagcc ggaggagaat gcgtgccagt tccagcgcct caatgcgcag    120
agacctgaca accgcattga atcggagggc ggttacattg agacttggaa ccccaacaac    180
caggagttcg aatgcgccgg cgtcgccctc tctcgcttag tcctccgccg caacgccctt    240
cgtaggcctt tctactccaa tgctccccag gagatcttca tccagcaagg aaggggatac    300
tttgggttga tattccctgg ttgtcctagc acatatgaag agcctgcaca acaaggacgc    360
cgatatcagt cccaaagacc accaagacgt ttgcaagaag aagaccaaag ccaacagcaa    420
```

-continued

```
caagatagtc accagaaggt gcaccgtttc aatgagggtg atctcattgc agttcccacc    480
ggtgttgctt tctggctgta caacgaccac gacactgatg ttgttgctgt ttctcttact    540
gacaccaaca acaacgacaa ccagcttgat cagttcccca ggagattcaa tttggctggg    600
aaccacgagc aagagttctt aaggtaccag caacaaagca gacaaagcag acgaagaagc    660
ttaccatata gcccatacag cccgcatagt cggcctagac gagaagagcg tgaatttcgc    720
cctcgaggac agcacagccg cagagaacga gcaggacaag aagaagaaga cgaaggtgga    780
aacatcttca gcggcttcac gccggagttc ctggaacaag ccttccaggt tgacgacaga    840
cagattgtgc aaaatctgtg gggcgagaac gagagtgaag aagagggagc cattgtgacg    900
gtgaggggag gcctcagaat cttgagccca gatggaacga gaggtgccga cgaagaagag    960
gaatacgatg aagatcaata tgaataccat gaacaggatg gaaggcgtgg cagggggaagc   1020
agaggcgggg ggaatggtat tgaagagacg atctgcaccg catgtgttaa aaagaacatt   1080
ggtggaaaca gatcccctca catctacgat cctcagcgct ggttcactca aaactgccac   1140
gatctcaacc ttctaatcct taggtggctt ggacttagtg ctgaatatgg aaatctctac   1200
aggaatgcat tgtttgtccc tcactacaac accaacgcac acagcatcat atatgcattg   1260
aggggacggg ctcacgtgca agtggtggac agcaacggca acagagtgta cgacgaggag   1320
cttcaagagg gtcacgttct tgtggtgcca cagaacttcg ccgtggctgg gaagtcccag   1380
agcgagaact tcgaatacgt ggcattcaag acagattcaa ggcccagcat agccaacttt   1440
gccggtgaaa actccttcat agataacctg ccggaggagg tggttgcaaa ttcatatggc   1500
ctcccaaggg agcaggcaag gcagcttaag aacaacaacc ccttcaagtt cttcgttcca   1560
ccttttcagc agtctccgag ggctgtggct taaaaacgac cagtatcttt tgcaagcgtg   1620
ttatccacta acataacttt ttgccacaaa tgaataatat aataataaga agaataatgt   1680
agttttaatt tttagtatga ataagaatac aaaggggcat tgatgccttt ttgtttaaga   1740
tcggaatgta acatatgtgc aatgagcaga tatggagaaa accttttgcg ggaaaaacat   1800
gaataataaa agaagttatg gtctcacgca aaaaaaaaaa aaaaaaaaaa aaa          1853
```

<210> SEQ ID NO 16
<211> LENGTH: 743
<212> TYPE: DNA
<213> ORGANISM: Arachis hypogaea

<400> SEQUENCE: 16

```
agaaagagaa gacaagatgt cgtggcaaac ctacgtcgat aaccaccttc tctgcgaaat     60
tgaaggcgac cacctctcct ccgccgcaat cctcggccaa gacggcggtg tttgggctca    120
gagctctcat ttccctcagt tcaagcctga ggaaattact gctatcatga acgactttgc    180
tgagcctgga tcgctcgccc ctaccgggtt gtacctcggt ggcaccaaat acatggttat    240
ccaaggtgaa cccggagcta tcattccagg gaagaagggt cctggtggtg ttaccattga    300
gaagacgaat caggcgttaa tcatcggaat ctacgataag ccaatgactc cggggcagtg    360
caacatgatt gttgaaaggc tgggtgatta tctcattgat acgggtcttt aagtcctctt    420
tgttatttct tgttatctgc ttgcttattt cactggctcc tatacgaggc ttcgcatcga    480
tgtgccaaga gaatgctcga ttgtagtgta ataatattaa ttgatgggta ttcaaaagtc    540
atgggatctg cgtctaggga agaagttatg gtgcttgaga agtgaatgat aactatcatc    600
tctgttgttg tgctttttag cgggtatctg tatacaattt acaagtggtt ttaatgctgt    660
gggcataaat gggcattaaa aaaaaaaaaa aaaaaaaaaa aaaaaaaaaa aaaaaaaaaa    720
```

-continued

```
aaaaaaaaaa aaaaaaaaaa aaa                                          743


<210> SEQ ID NO 17
<211> LENGTH: 627
<212> TYPE: DNA
<213> ORGANISM: Arachis hypogaea

<400> SEQUENCE: 17

gcacacgcct ccgcaatgag gcgcgagagg gggagacagg gggactcatc aagctgcgag     60

aggcaggttg acggggttaa cctcaagccc tgcgagcagc acataatgca gaggatcatg    120

ggcgagcaag agcagtacga ctcctacaat tttgggagta ctcgatcctc cgaccagcaa    180

cagaggtgct gcgatgagct gaacgagatg gagaacacac agagatgcat gtgcgaggca    240

ttgcagcaaa taatggagaa ccagtgcgat gggttgcagg acaggcaaat ggtgcagcac    300

ttcaagagag agctcatgaa cttgccccaa cagtgtaact ttggggcacc acagcgttgc    360

gatttggacg tgagtggcgg cagatgctag actcaaaaat tataatctgt gccaaaacaa    420

actagtagga agtagctgat attatgagct attatgtatg cttgtttcgt tgataataaa    480

tatcatcact gtatgaatgt ggtgataggt taggttatat gagcaccttc ggtgtgctct    540

tatggcttta cctatttttt gctactgcga agttttacca ccatgaaata aaagatcttc    600

cagttaaaaa aaaaaaaaaa aaaaaaa                                      627


<210> SEQ ID NO 18
<211> LENGTH: 712
<212> TYPE: DNA
<213> ORGANISM: Arachis hypogaea

<400> SEQUENCE: 18

atgatggtca agctcagcat cctggtagcc ctcctgggcg cccttcttgt cgtagcctcc     60

gcgacaagat gggatcccga tcgagggtcc agagggtcga gatgggacgc accgagcaga    120

ggggatgacc agtgccagag gcagttgcag agggcaaacc tgaggccctg tgaggaacac    180

atgaggcgaa gggtggagca ggagcaagag caagagcaag acgagtaccc gtacagccga    240

cggggatcca gaggacgaca acccggcgaa tctgacgaaa atcaagagca gaggtgctgc    300

aacgagctca accggttcca gaataaccaa aggtgcatgt gccaggcact tcaacagatc    360

ctccagaacc agagcttttg ggttccagca ggacaggagc cagttgcatc agatggagag    420

ggagctcagg aacttgcccc agaactgcgg gttcaggtca ccaagccgtt gcgacctttg    480

tagccgcacg ccctactaaa cagacgagca ctttgcgttt taatttgctt accccacaag    540

agaaatccaa tgatgatgat tgattgcttt tttacaagct atttctatgt ctatggtgtt    600

gtggtaacaa taaagatcat caccatttta tgtaatgatg atcgtattgt ccgtggcgaa    660

gttgtatggg gcactttgaa atgtgctttt atggcaaaaa aaaaaaaaaa aa           712
```